United States Patent
Cooney et al.

(10) Patent No.: US 9,493,815 B2
(45) Date of Patent: Nov. 15, 2016

(54) MICROARRAY BASED SAMPLE DETECTION SYSTEM

(71) Applicant: AKONNI BIOSYSTEMS, INC., Frederick, MD (US)

(72) Inventors: Christopher G. Cooney, Severn, MD (US); Peter Qiang Qu, New Market, MD (US); Alexander Perov, Germantown, MD (US); Jennifer Parker, Frederick, MD (US)

(73) Assignee: AKONNI BIOSYSTEMS, INC., Frederick, MD (US)

( * ) Notice: Subject to any disclaimer, the term of this patent is extended or adjusted under 35 U.S.C. 154(b) by 11 days.

(21) Appl. No.: 14/294,683

(22) Filed: Jun. 3, 2014

(65) Prior Publication Data
US 2014/0287954 A1    Sep. 25, 2014

Related U.S. Application Data

(63) Continuation of application No. 13/446,291, filed on Apr. 13, 2012, now Pat. No. 8,828,912, which is a continuation-in-part of application No. 12/886,201, filed on Sep. 20, 2010, now Pat. No. 8,623,789.

(60) Provisional application No. 61/272,397, filed on Sep. 21, 2009, provisional application No. 61/475,107, filed on Apr. 13, 2011.

(51) Int. Cl.
    *G01N 33/00* (2006.01)
    *C12Q 1/68* (2006.01)
    (Continued)

(52) U.S. Cl.
    CPC ........... *C12Q 1/68* (2013.01); *B01L 3/502715* (2013.01); *B01J 2219/00385* (2013.01); *B01J 2219/00576* (2013.01); *B01J 2219/00644* (2013.01); *B01J 2219/00722* (2013.01); *B01L 2200/026* (2013.01); *B01L 2200/0684* (2013.01);
    (Continued)

(58) Field of Classification Search
    CPC ........ G01N 1/34; B01L 2200/26; C12Q 1/68
    See application file for complete search history.

(56) References Cited

U.S. PATENT DOCUMENTS 5,741,700 A    4/1998    Ershov et al.
5,770,721 A    6/1998    Ershov et al.
(Continued)

FOREIGN PATENT DOCUMENTS

EP         1 762 300 A2      3/2007
WO       2007/136715 A2     11/2007
(Continued)

OTHER PUBLICATIONS

Extended European Search Report dated Sep. 10, 2014, in European Patent Application No. 12771527.4.
(Continued)

*Primary Examiner* — Sam P Siefke
(74) *Attorney, Agent, or Firm* — Michael Ye; Andrews Kurth Kenyon LLP

(57) ABSTRACT

A microarray assembly for detection of a target molecule is disclosed. The microarray assemblies comprise an array chamber having a microarray located therein and features that facilitate liquid movement within the array chamber. Also disclosed are methods for making the microarray assembly using rollable films and methods for detecting microarray spots using an internal control fluorophore in the array spot.

6 Claims, 10 Drawing Sheets

(51) Int. Cl.
*B01L 3/00* (2006.01)
*G01N 1/34* (2006.01)
(52) U.S. Cl.
CPC ....... *B01L 2200/10* (2013.01); *B01L 2300/069* (2013.01); *B01L 2300/0636* (2013.01); *B01L 2300/0681* (2013.01); *B01L 2300/087* (2013.01); *B01L 2300/0816* (2013.01); *B01L 2300/161* (2013.01); *B01L 2400/0406* (2013.01); *C12Q 1/6837* (2013.01); *G01N 1/34* (2013.01)

(56) References Cited

U.S. PATENT DOCUMENTS

| | | | |
|---|---|---|---|
| 5,922,604 | A | 7/1999 | Stapleton et al. |
| 5,981,734 | A | 11/1999 | Mirzabekov et al. |
| 6,605,213 | B1 | 8/2003 | Ammann et al. |
| 6,656,725 | B2 | 12/2003 | Mirzabekov et al. |
| 6,827,906 | B1 | 12/2004 | Bjornson et al. |
| 8,828,912 | B2 | 9/2014 | Cooney |
| 2004/0033590 | A1 | 2/2004 | Su et al. |
| 2005/0042146 | A1 | 2/2005 | Seto |
| 2005/0079101 | A1 | 4/2005 | Dufresne et al. |
| 2007/0031862 | A1 | 2/2007 | Chernov et al. |
| 2009/0111193 | A1 | 4/2009 | Cooney et al. |
| 2010/0261286 | A1 | 10/2010 | Kim et al. |
| 2010/0284859 | A1 | 11/2010 | Cooney et al. |
| 2011/0071055 | A1 | 3/2011 | Belgrader et al. |
| 2012/0149603 | A1 | 6/2012 | Cooney et al. |
| 2013/0157274 | A1 | 6/2013 | Belgrader et al. |

FOREIGN PATENT DOCUMENTS

| | | |
|---|---|---|
| WO | 2009/136892 A1 | 11/2009 |
| WO | 2011/011062 | 1/2011 |

OTHER PUBLICATIONS

Bengtsson, et al. "Microarray image analysis: background estimation using quantile and morphological filters," BMC Bioinformatics 2006, vol. 7, No. 96.
Notification Concerning Transmittal of International Preliminary Report on Patentability issued on Oct. 15, 2013, and Written Opinion of the International Searching Authority dated Nov. 30, 2012, in International Patent Application No. PCT/US2012/033498 (filed on Apr. 13, 2012).
Khodakov, et al., "An oligonucleotide microarray for multiplex real-time PCR identification of HIV-1, HBV, and HCV," BioTechniques, Feb. 2008, pp. 241-248, vol. 44, No. 2.
Pan'Kov, et al., "Kinetic Effects on Signal Normalization in Oligonucleotide Microchips with Labeled Immobilized Probes," Journal of Biomolecular Structure & Dynamics, 2009, pp. 235-244, vol. 27, No. 2.
Cooney, "SBIR Phase I: Reel-to-Reel Assembly of Lab-on-a-Film Diagnostic Tests Interim NSF Phase I Report," Akonni Biosystems, Jul. 15, 2011, pp. 1-12.
International Search Report issued in PCT/US2010/002568 dated Apr. 15, 2011.
Written Opinion issued in PCT/US2010/002568 dated Apr. 15, 2011.
File History of U.S. Pat. No. 8,623,789, issued on Jan. 17, 2014.
File History of U.S. Appl. No. 13/446,291, filed Apr. 12, 2012.
International Search Report, Written Opinion, International Patent Application No. PCT/US2015/063232, mailed Feb. 5, 2016.
Abe, C. et al., "Detection of Mycobacterium Tuberculosis in Clinical Specimens by Polymerase Chain Reaction and Gen-Probe Amplified Mycobacterium Tuberculosis Direct Test," Journal of Clinical Microbiology, Dec. 1993, vol. 31, No. 12, pp. 3270-3274.
Magcraft, "Permanent Magnet Selection and Design Handbook," Apr. 2007, pp. 1-16.
Sigma-Aldrich, "Dramatically Improve Mixing Results," 2009, vol. 3, No. 1, pp. 1-3.

| | 14 | 13 | 12 | 11 | 10 | 9 | 8 | 7 | 6 | 5 | 4 | 3 | 2 | 1 |
|---|---|---|---|---|---|---|---|---|---|---|---|---|---|---|
| 1 | | | | | | | | | | | | | | |
| 2 | | 0.1 nM | 1nM | 10nM | 0.1 uM | 1 uM | 10uM | 0.1 nM | 1nM | 10nM | 0.1 uM | 1 uM | 10 uM | |
| 3 | | 1 nM | | 31 | | | H | | | 31 | | | 1 nM | |
| 4 | | 10 nM | 14 | 35 | | | | | | 14 | 35 | | 0.1 uM | |
| 5 | | 0.1 uM | | 36 | | 29 | | | | | 36 | | 29 | 10 nM | |
| 6 | | 1 uM | | 37 | dN20 | | | 90 | | | 37 | dN20 | | 1 nM | |
| 7 | | 10 uM | | | | | | | CY3/5 | | | | | 0.1 nM | |
| 8 | | 0.1 nM | | | | | | CY3/5 | CY3/5 | | | | | 1 uM | |
| 9 | | 1 nM | | 31 | | | H | | | 31 | | | 0.1 uM | |
| 10 | | 10 nM | 14 | 35 | | | | | | 14 | 35 | | 10 nM | |
| 11 | | 0.1 uM | | 36 | | 29 | | | | | 36 | | 29 | 1 nM | |
| 12 | | 1 uM | | 37 | dN20 | | | 90 | | | 37 | dN20 | | 0.1 nM | |
| 13 | | 10 uM | 1nM | 10nM | 0.1 uM | 1 uM | 10uM | 0.1 nM | 1nM | 10nM | 0.1 uM | 1 uM | 10 uM | |
| 14 | | | | | | | | | | | | | | |

| | |
|---|---|
| 9 | mecA-P1 |
| 29 | PmecA3 (mecA GENE) |
| 14 | tufA- PanStaphHP5 (Staph GENUS) |
| 18 | S. AUREUS (SA5) |
| 19 | S. AUREUS (SA6) |
| 31 | S. AUREUS 7 (SA7) |
| | |
| 35 | SA-orfX1 |
| 36 | SA-orfX2a (types) |
| 37 | SA-orfX2b |
| | |
| 90 | M13#6 INTERNAL POSITIVE CONTROL |

*FIG. 6*

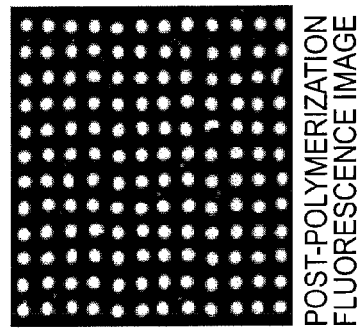
POST-POLYMERIZATION
FLUORESCENCE IMAGE
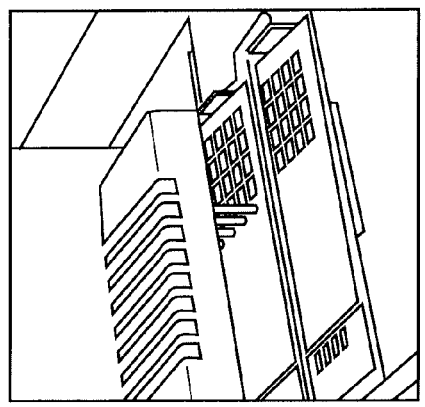
FIG. 7
POST-POLYMERIZATION
BRIGHT FIELD
PRE-POLYMERIZATION
BRIGHT FIELD
FIG. 8

FIG. 11

9.8 SEC 8.5 SEC 7.1 SEC

MICROARRAY BASED SAMPLE DETECTION SYSTEM

This application is a continuation of U.S. application Ser. No. 13/446,291, filed on Apr. 13, 2012, now U.S. Pat. No. 8,828,912, which is a continuation-in-part of U.S. patent application Ser. No. 12/886,201, filed on Sep. 20, 2010, now U.S. Pat. No. 8,623,789, which claims priority of U.S. Provisional Application No. 61/272,397, filed on Sep. 21, 2009, U.S. application Ser. No. 13/446,291, now U.S. Pat. No. 8,828,912 also claims the priority of U.S. Provisional Patent Application No. 61/475,107, filed on Apr. 13, 2011. The entirety of the aforementioned applications is incorporated herein by reference.

FIELD

The technical field is microfluidic systems and, in particular, microfluidic systems having a microarray for sample detection.

BACKGROUND

Microarrays are most prevalent in research laboratories as tools for profiling gene expression levels because thousands of probes can interrogate a single sample. Their utility is less ubiquitous as diagnostics for clinical, environmental, and agricultural applications despite their information density, redundancy, embedded controls (positive, negative), and analytical sensitivity. The barrier to adoption of microarrays as diagnostics tests is predominantly due to their operational complexity and cost (often hundreds of dollars per test), as well as technical problems associated with microfluidic devices containing a microarray, such as the unpredictable behavior of fluid flow caused by air bubbles in the microfluidic devices. For example, bubbles can clog channels, interfere with biochemical reactions (particularly those that require surface interactions), cause improper proportioning, interfere with optical reads, and result in unpredictable flow. Unpredictable flow is particularly a problem for systems that rely on steady diffusion of an analyte to a binding partner, such as an oligonucleotide or a capturing antibody. Accordingly, there still exists a need for microarray-based microfluidic detection systems that are designed to provide predictable fluid flow and can be manufactured at a low cost.

SUMMARY

One aspect of the present application relates to a microarray assembly for detection of a target molecule in a sample. In one embodiment, the microarray assembly comprises: an array chamber with a sample inlet at a first end, a sample outlet at a second end, a top interior surface, a bottom interior surface, side walls and a microarray located on the bottom interior surface; and a waste chamber that is in fluid communication with the outlet of the array chamber, wherein the array chamber comprises a hydrophilic interior surface positioned to facilitate complete filling of the array chamber by a water-based fluid and the continuous flow of the fluid from the sample inlet to the sample outlet and wherein the cross-sectional area at the first end of the array chamber is larger than the cross-sectional area at the second end of the array chamber.

In another embodiment, the microarray assembly comprises: an array chamber with a sample inlet, a sample outlet, a top interior surface, a bottom interior surface, side walls and a microarray located on the bottom interior surface; a waste chamber comprising a waste inlet and an absorbent material; and a channel having an expansion section with a first end proximate to the outlet of the array chamber and a second end proximate to the inlet of the waste chamber, wherein the top interior surface is a hydrophilic surface that facilitates complete filling of the array chamber by an aqueous fluid and wherein the cross-sectional area at the first end of the expansion section is smaller than the cross-sectional area at the second end of the expansion section.

In another embodiment, the microarray assembly comprises: an array chamber with a sample inlet at a first end, a sample outlet at a second end, a top interior surface, a bottom interior surface, side walls and a microarray located on the bottom surface; and a waste chamber that is in fluid communication with the outlet of the array chamber, wherein the array chamber comprises a hydrophilic interior surface positioned to facilitate complete filling of the array chamber by an aqueous-based fluid and channels with rectangular cross-sectional areas patterned onto the bottom interior surface and/or the top interior surfaces to promote drying.

Another aspect of the present application relates to a method for controlling the quality of manufacturing array elements in a microarray. The method comprises the steps of illuminating a microarray having a plurality of array spots with light waves to produce fluorescence from each array spot; measuring fluorescence intensity for each array spot wherein the fluorescence is produced by an internal quality control fluorophore; producing a fluorescent image of the microarray; determining information for each array spot based on the fluorescent image; and encoding the information in a barcode, memory device or RFID tag, wherein the barcode, memory device or RFID tag is associated with the microarray.

Another aspect of the present application relates to a method for making a microarray assembly. The method comprises the steps of unrolling a substrate film by one or more substrate film reels; printing microarrays onto the unrolled substrate film; laminating a spacer film on top of the printed substrate film, wherein the spacer film is pre-cut to provide space for an array chamber prior to the placing step and is placed on top of the printed substrate film by one or more spacer film reels; laminating a cover film on top of the spacer film to form a layered microarray structure; and cutting the layered microarray structure into individual microarray assemblies.

BRIEF DESCRIPTION OF THE DRAWINGS

The detailed description will refer to the following drawings:

FIG. 6 shows an array map with a serial dilution of Cy5 and Cy3 spots.

FIG. 7 shows an image of a blunt-pin print head.

FIG. 8 shows bright field images of arrays printed on a polyester thin film with the vacuum manifold before polymerization and after polymerization, as well as a fluorescence image of a Cy3 array.

FIG. 10 shows a fluorescence image following PCR of materials that were assembled with rollable materials including a polyester film that the array was printed on.

FIG. 11 is a composite of pictures showing a reel-to-reel printing setup with a BioDot Ultranon-contact array printer (top panel) and video frames of non-contact printing using the BioDot Ultra on a moving film that has not been chemically treated or modified (bottom panels).

DETAILED DESCRIPTION

Figure 1A:
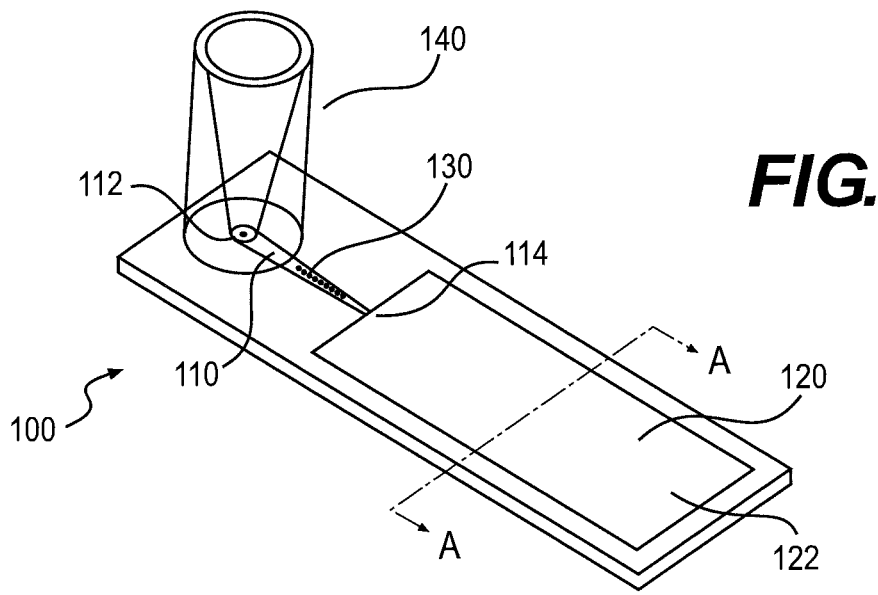
FIG. 1A is a schematic of an embodiment of a microarray assembly that contains a reservoir, a decreasing cross-sectional area array chamber, an array of spots, a waste chamber, and an absorbent.

This description is intended to be read in connection with the accompanying drawings, which are to be considered part of the entire written description of this invention. The drawing figures are not necessarily to scale and certain features of the invention may be shown exaggerated in scale or in somewhat schematic form in the interest of clarity and conciseness. In the description, relative terms such as "front," "back" "up," "down," "top" and "bottom," as well as derivatives thereof, should be construed to refer to the orientation as then described or as shown in the drawing figure under discussion. These relative terms are for convenience of description and normally are not intended to require a particular orientation. Terms concerning attachments, coupling and the like, such as "connected" and "attached," refer to a relationship wherein structures are secured or attached to one another either directly or indirectly through intervening structures, as well as both movable or rigid attachments or relationships, unless expressly described otherwise.

The term "microarray," as used herein, refers to an ordered array of spots presented for binding to ligands of interest. A microarray consists of at least two spots. The ligands of interest include, but are not limited to, nucleic acids (e.g., molecular beacons, aptamers, locked nucleic acids, peptide nucleic acids), proteins, peptides, polysaccharides, antibodies, antigens, viruses, and bacteria.

The term "hydrophilic surface" as used herein, refers to a surface that would form a contact angle of 45° or smaller with a drop of pure water resting on such a surface. The term "hydrophobic surface" as used herein, refers to a surface that would form a contact angle greater than 45° with a drop of pure water resting on such a surface. Contact angles can be measured using a contact angle goniometer.

The term "array chamber," as used herein, refers to an enclosed space around a microarray that has fluid communication with an inlet and an outlet either directly or indirectly. The array chamber, when filled with a liquid sample, allows the microarray to be submerged in the liquid sample so that target molecules in the liquid sample can maintain intimate contact with the microarray probes.

Microarray System Designed to Facilitate Fluid Flow within the System

One aspect of the present application relates to a microarray-based detection system comprising a microarray assembly comprising an array chamber with a sample inlet, a sample outlet and a microarray located therein, and a waste chamber that is in fluid communication with the array chamber. The array chamber has a hydrophilic surface positioned to facilitate complete filling of the array chamber and the fluid flow from the array chamber to the waste chamber. The hydrophilic surface contacts a liquid as it enters the array chamber from the sample inlet and allows complete filling of the array chamber. In certain embodiments, the array chamber is in the shape of an elongated channel of variable width and is directly connected to the waste chamber. In other embodiments, the array chamber is connected to the waste chamber through a waste channel.

Surface tension of a liquid sample or a reaction mixture often prevent the liquid sample or reaction mixture from completely filling a small space, such as the array chamber of a microarray system. Surface tension is the result of the attraction between the molecules of the liquid sample by various intermolecular forces. In the bulk of the liquid sample, each molecule is pulled equally in all directions by neighboring liquid molecules, resulting in a net force of zero. At the surface of the liquid sample, the molecules are pulled inwards by other molecules deeper inside the liquid and are not attracted as intensely by the molecules in the neighboring medium (be it vacuum, air or another fluid). Therefore all of the molecules at the surface are subject to an inward force of molecular attraction which can be balanced only by the resistance of the liquid sample to compression. This inward pull tends to diminish the surface area, and in this respect a liquid surface resembles a stretched elastic membrane. Accordingly, the liquid squeezes itself together until it has the locally lowest surface area possible. The net result is that the liquid sample may maintain a near-spherical shape inside the small space and does not fill the corners, especially square corners of the small space. The typical small gap that separates the cover from the microarray surface in an array chamber often compresses the liquid into a cylindrical shape.

In the case of microarray systems, the liquid that fills the array chamber is most likely an aqueous solution, such as a hybridization buffer or washing buffer. The surface tension of the aqueous solution may be overcome by coating at least a portion of the interior surface of the array chamber with a hydrophilic material. In some embodiments, the microarray is located on the bottom surface of the array chamber and the top surface, or at least a portion of the top surface, of the array chamber is coated with a hydrophilic coating.

Examples of the hydrophilic material include, but are not limited to, hydrophilic polymers such as polyethylene glycols, polyhydroxyethyl methacrylates, Bionite, poly(N-vinyl lactams), poly(vinylpyrrolidone), poly(ethylene oxide), poly (propylene oxide), polyacrylamides, cellulosics, methyl cellulose, polyanhydrides, polyacrylic acids, polyvinyl alcohols, polyvinyl ethers, alkylphenol ethoxylates, complex polyol mono-esters, polyoxyethylene esters of oleic acid, polyoxyethylene sorbitan esters of oleic acid, and sorbitan esters of fatty acids; inorganic hydrophilic materials such as inorganic oxide, gold, zeolite, and diamond-like carbon; and surfactants such as Triton X-100, Tween, Sodium dodecyl sulfate (SDS), ammonium lauryl sulfate, alkyl sulfate salts, sodium lauryl ether sulfate (SLES), alkyl benzene sulfonate, soaps, fatty acid salts, cetyl trimethylammonium bromide (CTAB) a.k.a. hexadecyl trimethyl ammonium bromide, alkyltrimethylammonium salts, cetylpyridinium chloride (CPC), polyethoxylated tallow amine (POEA), benzalkonium chloride (BAC), benzethonium chloride (BZT), dodecyl betaine, dodecyl dimethylamine oxide, cocamidopropyl betaine, coco ampho glycinate alkyl poly(ethylene oxide), copolymers of poly(ethylene oxide) and poly(propylene oxide) (commercially called Poloxamers or Poloxamines), alkyl polyglucosides, fatty alcohols, cocamide MEA, cocamide DEA, cocamide TEA.

In some embodiments, one or more surfactants are mixed with reaction polymers such as polyurethanes and epoxies to serve as a hydrophilic coating. In other embodiments, the top surface or the bottom surface of the array chamber is made hydrophilic by surface treatment such as atmospheric plasma treatment, corona treatment or gas corona treatment.

Examples of hydrophilic tape include, but are not limited to, Adhesives Research (AR) tape 90128, AR tape 90469, AR tape 90368, AR tape 90119, AR tape 92276, and AR tape 90741 (Adhesives Research, Inc., Glen Rock, Pa.). Examples of hydrophilic film include, but are not limited to, Vistex® and Visguard® films (Film Specialties Inc., Hillsborough, N.J.), and Lexan HPFAF (GE Plastics, Pittsfield, Mass.). Other hydrophilic surfaces are available from Surmodics, Inc. (Eden Prairie, Minn.), Biocoat Inc. (Horsham, Pa.), Advanced Surface Technology (Billerica, Mass.), and Hydromer, Inc. (Branchburg, N.J.).

In some embodiments, the hydrophilic tape or film has sufficient transparency to allow optical interrogation of the microarray from the top of the array chamber.

The microarray can be any type of microarray, including but not limited to oligonucleotide microarrays and protein microarrays. In one embodiment, the microarray is an antibody array and the microarray system is used for capturing and labeling target antigens. In one embodiment, the microarray is formed using the printing gel spots method described in e.g., U.S. Pat. Nos. 5,741,700, 5,770,721, 5,981,734, 6,656,725 and U.S. patent application Ser. Nos. 10/068,474, 11/425,667 and 60/793,176, all of which are hereby incorporated by reference in their entirety. In certain embodiments, the microarray comprises a plurality of array spots printed on an array substrate that forms the bottom of the array chamber. In some embodiments, the array substrate is glass or plastic.

In certain embodiments, the array spots contain an internal control fluorophore having an emission spectrum that is different from those of the fluorophores associated with target molecules (i.e., the target molecules will be labeled with fluorophores that have emission spectra that are different from the emission spectrum of the internal control fluorophore). This internal control may be analyzed in the field or during manufacturing to improve quality. The internal control would provide a quantitative means of assessing the fluorescence intensity (e.g., average, mean or integral) of the spot, which may vary due to drop diameter, morphology, porosity, or any factor that may change the reproducibility from spot to spot. Factors that influence these properties include UV dosage, temperature, surface properties, synthesis, viscosity, condensation, washing (i.e., due to effects caused by differences in temperature, viscosity, flow rate, stringency or anything that may influence the removal or distortion of the spots), depth of pin immersion in the polymer solution for pin printing technologies or any property that could influence the morphology of gel elements or concentration of the probes therein. Imaging in the field would additionally account for: misuse by the user, destruction of the gel elements due to poor handling, washing of the gel elements, increased brightness due to the presence of salts, thermocycling, high temperature conditions decreasing fluorescent yield, low temperature condition increasing fluorescent yield, shelf-life degradation, and/or anything that contributes to the change in fluorescence signal following the initial QA/QC during manufacture of the arrays.

Examples of fluorophores include, but are not limited to, pyrene, 7-methoxycoumarin, cascade blue, 6-MI, 3-MI, 7-aminocoumarin-X (AMCA-X), 6-MAP, pacific blue, marina blue, dimethylaminocoumarin, BODIPY 493/503, BODIPY-FI-X, DTAF (5-DTAF), 6-FAM (fluorescein), dansyl-X, Oregon green 500, Oregon green 488 (5 isomer), rhodol green, Oregon green 514, rhodamine green-X, NBD-X, TET, 2'4'5'7'-tetrabromosulfonefluorescein, BODIPY-FI BR$_2$, BODIPY-R6G, 6-JOE, BODIPY 530/550, HEX, carboxyrhodamine 6G, BODIPY 558/568, BODIPY-TMR-X, PyMPO, BODIPY 564/570, Cy3, TAMRA-X, Rhodamine Red-X, BODIPY 576/589, BODIPY 581/591, Texas Red-X, Cy3.5, ROX, BODIPY-TR, Syto-81, Cy5, napthofluorescein, Cy5.5, VIC, SYBR green I, and SYBR green II.

In other embodiments, the internal control is a colorimetric signal change, which is distinct from spot to spot. In other embodiments, the internal control is a chemiluminescence signal change, which is distinct from spot to spot. In yet other embodiments, the internal control is an electrochemical signal change, which is distinct from spot to spot.

In certain embodiments, the array spots are gel spots containing a first fluorophore (e.g., Cy5). The targets in the sample are labeled with a second fluorophore (e.g., Cy3) during PCR and subsequently hybridize to probes that are covalently attached to the gel drop polymer. The first fluorophore has a different emission peak than the second fluorophore. In this setting, the first fluorophore (e.g., Cy5) serves to allow exact location of the gel spots with an imaging system that can detect both the first and the second fluorophores (e.g., Cy3 and Cy5).

In some embodiments, the imaging system is a component of the microarray-based sample detection system. In other embodiments, the imaging system is part of a machine vision system used during manufacturing the microarray assembly such that the coordinates of each spot can be precisely determined during inspection. These coordinates are uploaded onto a barcode or RFID tag that is attached to the microarray assembly for future analysis. For this approach to be effective, the first fluorophore (i.e., the internal control fluorophore) coordinates require that the second fluorophore (i.e., the target fluorophore) reference fiducials are included as part of the assembly map, so that the grid can be placed. However, unlike conventional scheme that either attempt to place a grid based on precisely spaced spots or require two color fluorescence imagers, the disclosed scheme uses the coordinates from the barcode to place fixed circles for spot detection. Location of the first fluorophore (i.e., the internal control fluorophore) spots can be used with a thresholding algorithm to find the centers, which are then used for placement of fixed circles.

A benefit of the use of machine vision to identify spots is that the same system can be used to reject spots without rejecting the entire microarray, which would increase yield. Spots can be rejected based on a number of criteria such as internal control fluorescence intensity values that are out of bounds, asymmetry, and diameter. Therefore, some embodiments of the present application relate to a method for controlling the quality of manufacturing array elements in a microarray, comprising: illuminating a microarray having a plurality of array spots with light waves to produce fluorescence from each array spot; measuring fluorescence intensity for each array spot wherein the fluorescence is produced by an internal quality control fluorophore; producing a fluorescent image of the microarray; determining information for each array spot based on the fluorescent image; and encoding the information in a barcode, memory device or RFID tag, wherein the barcode, memory device or RFID tag is associated with the microarray. The information for each array spot may comprise the location of each spot, the fluorescence intensity of each spot, the diameter of each spot and the morphology of each spot. A microarray image analysis may be conducted by placing fixed circles for each microarray spot on the image of a microarray using the spot location information determined based the internal control fluorescence.

In one embodiment, the present application provides a method for microarray image analysis. The method comprises the steps of obtaining an image of a microarray, placing a fixed spot border circle around each microarray spot on the image of the microarray based on the array spot location information obtained through the internal control fluorescence in the array spots as described above; measuring a target fluorescence intensity within the fixed spot border circle for each array spot, and determining the amount of a target molecule in a sample based on the ratio of the target fluorescence intensity to the internal fluorescence intensity at each array spot.

In another embodiment, a method for microarray image analysis includes the following steps: determining a target fluorescence intensity for a target spot in a microarray; determining an internal fluorescence intensity for the target spot in the microarray; determining a signal strength for the target spot in the microarray, wherein the signal strength is a ratio of the target fluorescence intensity to the internal fluorescence intensity, wherein the internal fluorescence intensity for the target spot in the microarray is determined as described earlier.

In another embodiment, the present application provides a method for imaging array elements in a microarray. The method includes the steps of illuminating a microarray having a plurality of array spot with light waves of a first wavelength to produce fluorescence from an internal control fluorophore; determining location of array spots of the microarray based on fluorescence produced by the internal control fluorophore (control fluorescence); illuminating the microarray with light waves of a second wavelength to produce fluorescence from a target fluorophore that is associated, directly or indirectly, to a target molecule that binds to an array spot; measuring fluorescence produced by the target fluorophore (target fluorescence); and determining the amount of the target molecule in the sample based on the control fluorescence intensity-to-target fluorescence intensity ratio in relevant array spots.

The waste chamber can be of any shape and typically has a volume that is greater than the volume of the array chamber. In one embodiment, the waste chamber is formed in a gasket tape which is then attached to the substrate on which the microarray is printed. In yet another embodiment, the substrate has a cut-out on its top surface. The cut-out has a size and position that match the size and position of the waste chamber in the gasket so that the waste chamber, once formed between the substrate and the gasket, would have a thickness that is greater than the thickness of the array chamber. In another embodiment, the substrate is made of a plastic material so that a cut-out may be easily made on the substrate. In yet another embodiment, both the array chamber and the waste chamber are formed in the substrate without using the gasket. The waste chamber, however, may have a depth that is greater than the depth of the array chamber.

In one embodiment, the waste chamber contains an absorbent that, once in contact with the liquid in the array chamber, wicks the liquid from the array chamber, therefore allowing the microarray to be read in a dry state.

The absorbent can be any material capable of retention of a relatively large volume of liquid. In one embodiment, the absorbent is made of an aggregate of fibers. In another embodiment, the absorbent is a nonwoven fabric produced in a through-air bonding process. The constituent fibers of the nonwoven fabric can be hydrophilic synthetic fibers, natural cellulose fibers of pulp or the like, or regenerated cellulose fibers. The fibers may be coated or infiltrated with a surfactant or a hydrophilic oil to improve liquid absorbance. Not limited to the through-air bonding process, the nonwoven fabric for use herein may be produced in any other process such as a spun-bonding process, an air laying process, a spun-lacing process, etc. In one embodiment, the absorbent is a cellulose paper (C048) from Millipore (Billerica, Mass.).

In some embodiments, the waste chamber is vented to the atmosphere through a vent. In one embodiment, the vent is created by simply punching a hole in the cover of the waste chamber.

In another embodiment, the liquid in the array chamber is removed by forcing the liquid inside the reservoir into the array chamber and establishing a contact between the liquid in the array chamber and the absorbent in the waste chamber. The contact may be established by applying a pressure to the liquid in the array chamber to push the liquid out of the array chamber or by applying suction at a vent of the waste chamber to pull the liquid out of the array chamber. A pressure to the liquid in the array chamber may be generated by applying a pressure through a check valve (e.g., using a pipette or a syringe). If the array chamber is covered only with a hydrophilic tape or a hydrophilic film, a pressure to the liquid inside the array chamber may be generated by simply pressing the hydrophilic tape or film that form the top surface of the array chamber. Alternatively, the contact between the liquid in the array chamber and the absorbent may be established by placement of the absorbent near the array chamber such that the absorbent touches the liquid inside the channel.

Once a contact is established, the liquid in the array chamber is wicked into the absorbent in the waste chamber through the array chamber. The flow rate of the liquid is determined by the size of the array chamber, the surface tension and viscosity of the liquid, and the wicking rate of the absorbent. In addition, the flow rate decreases as the absorbent becomes more saturated.

In another embodiment, the microarray system further contains a one-way valve for introducing a liquid (e.g., a sample, a PCR buffer with target, a hybridization buffer, or a washing buffer) into the array chamber. The sample is introduced into the array chamber through the one-way valve to prevent environmental contamination, which is an important concern in certain applications such as the detection of biological warfare agents. The one-way valve can be a check valve, a dome valve or a duckbill valve that is placed at the inlet of the array chamber. Dome valves of various sizes are commercially available e.g., from Minivalve International (Yellow Springs, Ohio).

In some embodiments, the side walls of the array chamber are hydrophobic to trap bubbles. In other embodiments, the array chamber has a hydrophilic cover that is configured such that a hydrophilic region is created near the outlet of the array chamber. In a related embodiment, the hydrophilic region is created with hydrophilic gel elements.

In another embodiment, the inlet of the array chamber contains a pierceable membrane/tape or a dome valve, check valve or duckbill valve to allow washing to occur without causing the content inside the array chamber to be liberated from the microarray assembly.

In another embodiment, the microarray system further contains a reservoir for introducing a liquid into the array chamber. In a related embodiment, the reservoir is loosely bound to the device so that it can be snapped off and removed for imaging in conventional microarray or colorimetric readers. In another embodiment, the array chamber is connected to multiple waste chambers to ensure that wicking occurs at the appropriate interval.

In the event that an air bubble is introduced into the array chamber, the air bubble may be lodged in the array chamber and partially or completely block liquid flow in the array chamber. The air bubble may also stop the wicking action of the absorbent if the air bubble is located right at the interface of the liquid and the absorbent. In some embodiments, the array chamber of the microarray assembly is shaped to facilitate bubble movement within the array chamber. In some embodiments, the array chamber has a cross-sectional area that decreases continuously, or in a stepwise fashion, from one end of the chamber to the other end of the chamber so as to facilitate liquid movement, as well as the bubble movement, from the inlet of the array chamber to the outlet of the array chamber.

FIG. 1A shows an embodiment of a microarray assembly 100 designed to facilitate the removal of air bubbles in the array chamber. The microarray assembly 100 comprises a funnel-shaped array chamber 110 spanning from a sample inlet 112 to an outlet 114, which opens into a waste chamber 120 having an absorbent 122. The microarray chamber 110 contains a plurality of microarray spots 130 that are positioned on top of a substrate 150 (see FIG. 1C), which also forms the bottom of the array chamber 110. In certain embodiments, the array chamber 110 is connected to a reservoir 140. In this embodiment, the array chamber 110 has a progressively decreasing cross-sectional area towards the direction of the waste chamber 120, thus the capillary pressure continuously increases as the liquid in the array chamber 110 approaches the waste chamber 120. The pressure difference leads to liquid movement towards the absorbent 122 in the waste chamber 120. In other words, the shape of the array chamber 110 provides continuous wicking of a liquid in the array chamber 110 in the direction of the waste chamber 120 until the liquid reaches the absorbent 122 in the waste chamber 120. In some embodiments, the cross section area at the inlet end of the array chamber 110 is at least 2-times, 3-times, 4-times or 5-times larger than the cross section area at the outlet end of the array chamber 110.

In one embodiment, the array chamber 110 has a trapezoid shape with dimensions that range from 0.5 to 20 mm on the inlet end and 0.1 to 5 mm on the outlet end. In another embodiment, the array chamber 110 comprises a series of steps that have a progressively smaller cross-sectional area from the inlet end to the outlet end. These features are designed to have a small radius of curvature on the advancing front compared to the receding front, so that air bubbles in the array chamber 110 advance towards the waste chamber 120, preventing the aforementioned issues associated with bubbles.

Figure 1B:
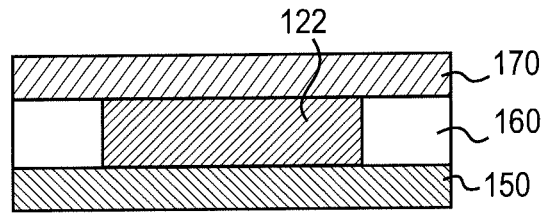
FIG. 1B is a cross-sectional view of the array assembly in FIG. 1A.

FIG. 1B is a cross-sectional view of the microarray assembly 100 along line AA in FIG. 1A. In this embodiment, the microarray assembly 100 comprises the array substrate layer 150, the spacer layer 160 and the cover layer 170. In one embodiment, the spacer layer is a double-sided tape, such as an inner gasket tape, with a thickness of 0.25 mm (available from 3M, Part No. 9087). In other embodiments, the array substrate layer 150 is injection molded plastic with features that create the walls of the array chamber 110 and a pocket for the waste chamber 120 and there is no spacer layer 160 in these embodiments.

In other embodiments, a hydrophilic film is laminated to a plastic array substrate 150 with heat and/or pressure to form a hydrophilic surface on which the microarray is printed. The lamination may be performed with laser welding or ultrasonic welding.

Figure 2:
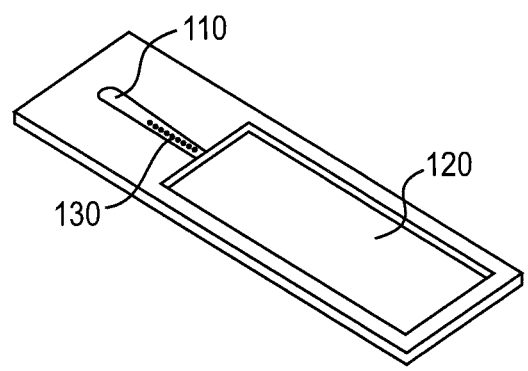
FIG. 2 is a close-up view of the array chamber showing a linear array of spots printed at the bottom of the chamber that has a decreasing cross-sectional area.

FIG. 2 provides a close-up view of the funnel shaped array chamber 110 of FIG. 1A. As shown in FIG. 2, the decreasing chamber width or the "wedge" shape of the array chamber enables increasing capillary pressure on the side of the waste chamber 120. This configuration allows bubbles to flow through the array chamber and avoids clogging of the array chamber 110 by air bubbles. This funnel-shaped narrow chamber 110 also facilitates the diffusion of the target molecules in a sample to the array spots 130. In some embodiments, the sample is loaded into the reservoir 140 and continuously flows through the array chamber 110 and into the waste chamber 120.

In some embodiments, the microarray spots 130 are arranged in the form of multiple strips (e.g., protein strip array) that are perpendicular to the flow in the array chamber 110 so as to improve interaction between the target molecule in the sample and the array elements. In one embodiment, a protein array or a protein strip array is printed inside the array chamber 110. Proteins extracted from a sample are loaded into the reservoir 140 and flow through the array spot 130 or strip 130 in a continuous fashion to enter the waste chamber 120.

A person of ordinary skill in the art would understand that the microarray assembly 100 may have many variations. For example, the entire microarray assembly 100 may be molded in two halves creating a parting line that spans the center line of the reservoir 140, the substrate 150 and the waste chamber 120. The parting line may take a contoured path to allow easy access for hydrophilic surface treatment of the top side of the array chamber 110, and/or printing the array spots 130 on the top surface of the substrate 150. The top half of the array assembly may be treated to be hydrophilic such as with a plasma treatment, a surfactant or any of the techniques described above, and bonded into place using ultrasonic welding, laser welding, snap fit design, glue, tape, or any bonding method. In some embodiments, the cover layer 170 is sized to cover only the chamber areas but not the complete top surface of the microarray assembly 100.

Figure 3:
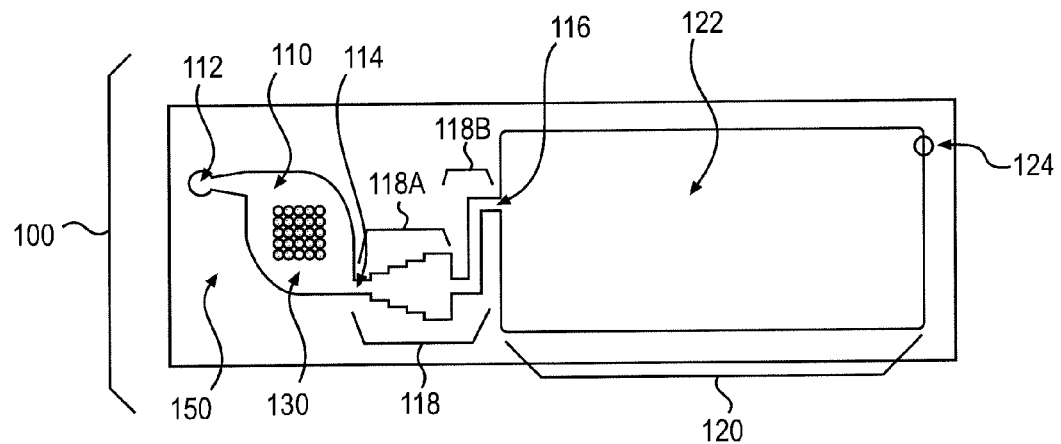
FIG. 3 is a microarray assembly with an expanding channel connecting the array chamber to the waste chamber.

FIG. 3 shows another embodiment of a microarray assembly 100 designed to facilitate the removal of air bubbles in the array chamber 110 as well as maintain the sample within the array chamber 110 during prolonged exposure to extreme temperatures (up to 95° C.). In this embodiment, the microarray assembly 100 comprises an array chamber 110 having a sample inlet 112, a sample outlet 114 and a plurality of microarray spots 130 positioned on top of the substrate 150, a waste chamber 120 having an absorbent 122, an inlet 116, and a vent 124 and a channel 118 that connects the sample outlet 114 of the array chamber 110 to the inlet 116 of the waste chamber 120. In this embodiment, the channel 118 has an expansion section 118A and a switchback section 118B. The expansion section 118A has progressively increasing cross-sectional area towards the direction of the waste chamber 120, so that air bubbles in the array chamber 110, once entering the channel 118, are trapped on the side walls of the section 118A and do not block fluid flow in the channel 118. The expansion section 118A helps to pin the contact line of the liquid on the convex corners of the section during sample expansion when the array chamber 110 is exposed to high temperatures. In one embodiment, the sidewall of channel 118 is hydrophobic to trap bubbles. In some embodiments, the cross-sectional area at the waste chamber end of the channel 118A is at least 2-times, 3-times, 4-times or 5-times larger than the cross-sectional area at the array chamber end of the channel 118A. In some embodiments, the switchback section 118B contains two turns to form an S-shaped or Z-shaped channel section. In one embodiment, the two turns are 90° turns.

Figure 4A:
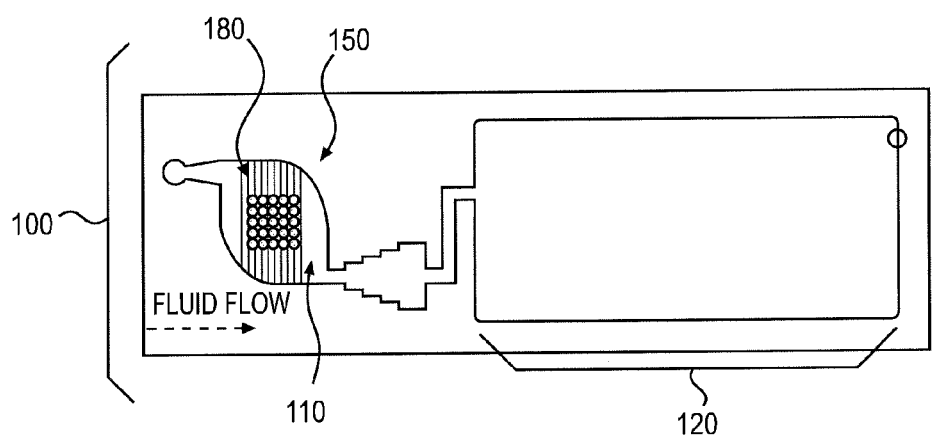
FIG. 4A is a schematic showing an array chamber with small rectangular channels that are perpendicular to the direction of the liquid flow inside the chamber.
Figure 4B:
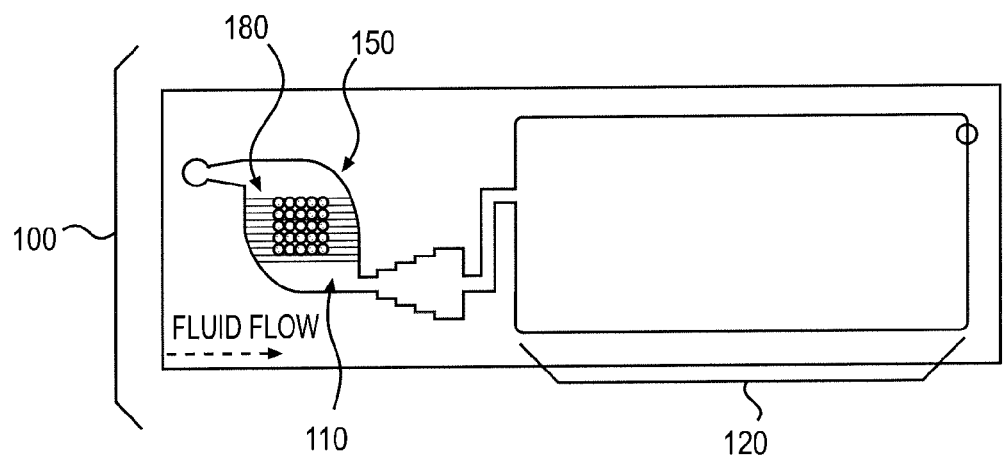
FIG. 4B is a schematic showing an array chamber with small rectangular channels that are parallel to the direction of the liquid flow inside the reaction chamber.
Figure 4C:
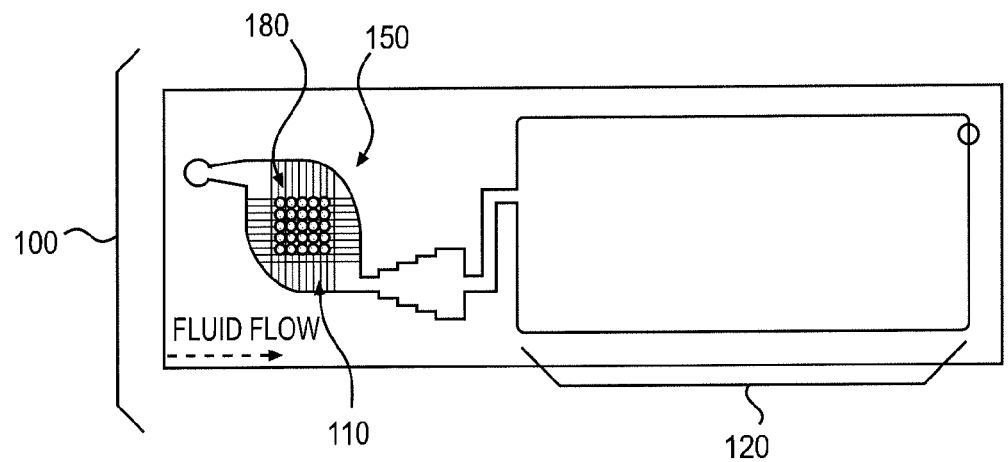
FIG. 4C is a schematic showing an array chamber with small rectangular channels that are perpendicular or parallel to the direction of the liquid flow within the reaction chamber.
Figure 4D:
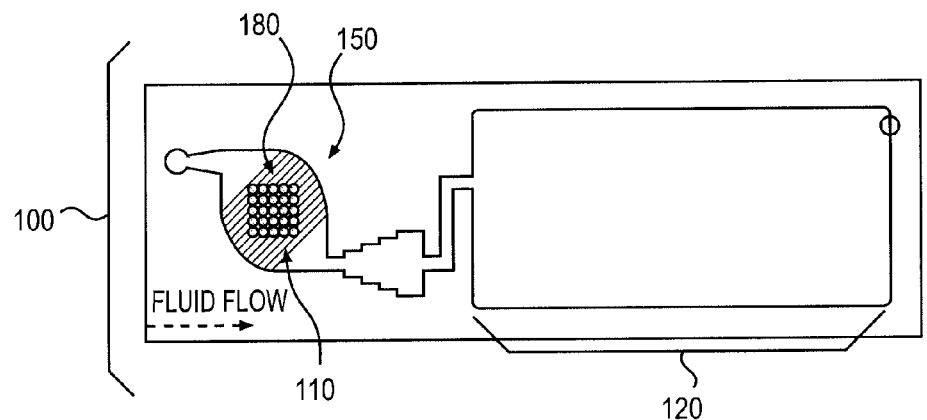
FIG. 4D is a schematic showing an array chamber with small rectangular channels that form an angle to the direction of the liquid flow within the reaction chamber.

In other embodiments, the array chamber 110 is fabricated with small rectangular channels 180 (i.e., channels with rectangular cross-sectional areas) that are perpendicular to the direction of the flow to provide a means of drying the array (see FIG. 4A). These channels 180 have sharp corners that result in small radius of curvature of the liquid-air interface, and thus provide high capillary pressures that advance liquids along the side walls and to the waste chamber 120. In another embodiment, the rectangular channels 180 are parallel to the liquid flow path (see FIG. 4B). In another embodiment, the rectangular channels 180 are both parallel and perpendicular to the liquid flow path (see FIG. 4C). In another embodiment the rectangular channels 180 intersect the liquid flow path at angles that range from 30 to 120 degrees (see FIG. 4D). In another embodiment, the top surface of the substrate 150 is roughened to provide the same wicking action along the crevices of the surface.

The top surface could also be roughened such that there are square microchannels that are parallel, intersect, perpendicular, or some or all of these. The contact angle at the corners should be lower than 90 degrees so as to advance the liquid along these channels towards the waste chamber (absorbent). This approach is similar to that of the tracheids (square capillaries) in conifer trees that allow liquid to advance up the length of trees, overcoming the effects of hydrostatic pressure Detection of Target Molecules with the Microarray Assembly Another aspect of the present application relates to a method of using the microarray assembly described above to detect a target molecule in a sample. The sample can be any biological sample, such as a swab, nasopharyngeal aspirate or whole blood sample. The total nucleic acids may be isolated using techniques well-known to a person of ordinary skill in the art. In one embodiment, the total nucleic acids are isolated with commercially-available nucleic acid isolation reagents or kits, such as the Qiagen reagents. In another embodiment, the total nucleic acids are isolated with a sample preparation device developed by Akonni Biosystems. The generalized sequence of events for Akonni's sample preparation methods includes denaturing the sample in a lysis buffer; continuous perfusion of the lysed sample over the sample preparation device; washing and eluting the nucleic acids from the sample preparation device.

The isolated nucleic acids are loaded into the microarray system and amplified within the microarray assembly using methods well-known to one skilled in the art. After amplification, the microarray assembly is incubated for a period of time at a desired temperature (e.g., 10-60 min at 50-65° C.) to allow the amplicons to hybridization to the microarray. After incubation, the microarray system is washed (e.g., with water) and imaged on a microarray reader (e.g., Akonni's portable microarray reader). In one embodiment, the microarray system is dried prior to imaging. In another embodiment, the drying procedure is accomplished with acetone introduction to the array chamber and/or heating the array chamber. In another embodiment, amplification of the isolated nucleic acids and labeling of the amplification products occur in an asymmetric PCR master mix containing fluorescently labeled "reverse" primers in large excess (e.g., 5-20 fold excess) over unlabeled, "forward" primers. This strategy generates predominantly single-stranded targets with a single label on their 5' end.

The array test can be performed with many variations. In one embodiment, the amplified product remains in the reaction chamber after hybridization and there is no washing before imaging of the microarray. In another embodiment, the amplified product remains in the array chamber, and the array spots are imaged in real-time during hybridization in order to show growth curves as described by Khodakov et al., 2008. In yet another embodiment, the array chamber supports a series of incubation and wash steps for multi-step assays such as ELISAs. In one embodiment, the incubation step is performed under periodic or continuous vibration to improve interaction between the array elements and the target proteins.

Manufacturing of the Microarray Assembly

Another aspect of the instant application relates to a method for manufacturing microarray assemblies having a substrate layer, a spacer layer and a cover layer using rollable thin film materials and reel-to-reel equipment. Briefly, rollable film materials are used for the substrate layer, the spacer layer and the cover layer of the microarray assembly. The films are layered together by unraveling several reels on top of one another, creating a sandwich of desired components, which are cut to size at the end of the manufacturing line. Specifically, a rollable substrate film is advanced onto a manufacturing platform. Array spots are printed onto the film, forming microarrays with a fixed interval between arrays. The printed substrate film is then laminated with a rollable spacer tape that has been pre-cut with a separate reel-to-reel manufacturing method to create space for the array chamber. A rollable cover film is then laminated on top of the spacer film to seal off the array chamber. In some embodiments, the rollable spacer tape is pre-cut to create space for the array chamber and one or more waste chambers. An absorbent is placed into each waste chamber prior to the lamination of the cover film to the spacer film. The virtue of this manufacturing method is that high volume production can be very cost effective because with standard production equipment, assembly of the microarray assemblies can be completely automated at very high speeds.

The substrate film can be any thin film having a surface that has double bonded carbon atoms. Preferably, the substrate film has a hydrophobic surface. Examples of the substrate film include, but are not limited to, polyester films, polyester/polycarbonate blend films, polytetrafluoroethylene, polyethylene, polyetherimide, polyether ether ketone, and polystyrene. In some embodiments, the substrate film has a thickness in the range of 20-200 microns, preferably 50-125 microns.

The spacer film can be any double-sided tape with a desired thickness. In certain embodiments, the spacer film is made from a hydrophobic material and has a thickness in the range of 20-500 micron, preferably 100-300 microns. Examples of the spacer film include, but are not limited to, polyester films, polyester/polycarbonate blend films, polypropylene, polycarbonate, acetal, poly(methyl methyacrylate), 256M tape from Adchem, and polytetrafluoroethylene. The cover film can be any thin film with a hydrophilic surface. Examples of hydrophilic film include, but are not limited to, Vistex® and Visguard® films (Film Specialties Inc., Hillsborough, N.J.), and Lexan HPFAF (GE Plastics, Pittsfield, Mass.). Other hydrophilic surfaces are available from Surmodics, Inc. (Eden Prairie, Minn.), Biocoat Inc. (Horsham, Pa.), Advanced Surface Technology (Billerica, Mass.), and Hydromer, Inc. (Branchburg, N.J.).

In some embodiments, the cover film has a thickness in the range of 25-250 microns, preferably 50-150 microns.

In some embodiments, the microarray is a gel spot microarray printed onto the substrate film with a non-contact microarray printer (e.g., a piezoelectric printer) that allows for printing on a moving film. In some embodiments, the gel spots comprise probes, such as protein probes or nucleotide probes that are covalently cross-linked to the polymer backbone by UV-induced co-polymerization.

Figure 5:
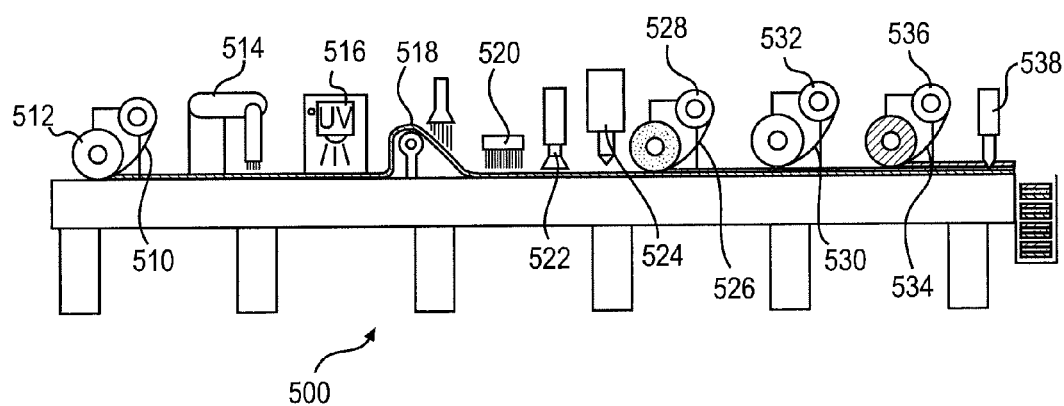
FIG. 5 shows a schematic of a continuous assembly line for manufacturing lab-on-a-film devices.

FIG. 5 shows an embodiment of a reel-to-reel assembly line for the manufacturing of the microarray device of the present application. Briefly, a substrate film 510 is laid onto the assembly line 500 by the substrate film reel 512. A gel spot printer 514 prints array spots onto the substrate film 510. Probes in the gel spots are covalently cross-linked to the polymer backbone by UV illumination. In one embodiment, the crosslinking is accomplished via a single-step, Argon-atmosphere, UV-induced co-polymerization process in a UV chamber 516. In one embodiment, the thin films are held in place using the inherent tension between reels on the system. This improves UV illumination uniformity on the surface of the thin film by keeping the films flat in the UV chambers during polymerization. The crosslinked microarray is washed at the wash station 518, dried by air knives 520 and examined by the quality control (QC) camera 522. Defective arrays can be marked by a reject marker 524 and a spacer film 526 is laminated onto the substrate film 510 by the spacer tape reel 528. The spacer film 526 can be pre-cut prior to lamination to create space for an array chamber and one or more waste chambers. Absorbents 530 are then added to the waste chambers using, such that size-on precut pieces of absorbent with an adhesive backing are placed in the open waste chamber via the absorbent reel 532. A cover film 534 is then laminated on top of the substrate/spacer layer structure by the cover film reel 536. The assembled layer structure is then cut by the guillotine 538 to produce individual microarray assemblies.

EXAMPLES

Example 1

Method for Compensating Microarray Printing Variations

Gel drop microarrays with Cy3 and Cy5 fluorophores were printed on ten separate slides according to the following assembly map. The following steps are used for printing the microarray: (1) prepare the appropriate Cy3/Cy5 oligo mixture and dry it down on a CentriVap, (2) prepare a copolymer solution (monomer+cross-linker+glycerol+buffer), (3) dissolve the dried oligo in copolymer solution, (4) place solution into a source plate, and (5) use the source plate for array printing/polymerization/washing.

Assembly Map

|    | 1 | 2 | 3 | 4 | 5 | 6 |
|----|---|---|---|---|---|---|
| 1  | Cy3:Cy5(1:1) | Cy3:Cy5(1:1) | Cy3:Cy5(1:1) | Cy3:Cy5(1:1) | Cy3:Cy5(1:1) | Cy3:Cy5(1:1) |
| 2  | Cy3:Cy5(1:1) | Cy3:Cy5(1:1) | Cy3:Cy5(1:1) | Cy3:Cy5(1:1) | Cy3:Cy5(1:1) | Cy3:Cy5(1:1) |
| 3  | Cy3:Cy5(1:1) | Cy3:Cy5(1:1) | Cy3:Cy5(1:1) | Cy3:Cy5(1:1) | Cy3:Cy5(1:1) | Cy3:Cy5(1:1) |
| 4  | Cy3:Cy5(1:1) | Cy3:Cy5(1:1) | Cy3:Cy5(1:1) | Cy3:Cy5(1:1) | Cy3:Cy5(1:1) | Cy3:Cy5(1:1) |
| 5  | Cy3:Cy5(1:1) | Cy3:Cy5(1:1) | Cy3:Cy5(1:1) | Cy3:Cy5(1:1) | Cy3:Cy5(1:1) | Cy3:Cy5(1:1) |
| 6  | Cy3:Cy5(1:1) | Cy3:Cy5(1:1) | Cy3:Cy5(1:1) | Cy3:Cy5(1:1) | Cy3:Cy5(1:1) | Cy3:Cy5(1:1) |
| 7  | Cy3:Cy5(1:1) | Cy3:Cy5(1:1) | Cy3:Cy5(1:1) | Cy3:Cy5(1:1) | Cy3:Cy5(1:1) | Cy3:Cy5(1:1) |
| 8  | Cy3:Cy5(1:1) | Cy3:Cy5(1:1) | Cy3:Cy5(1:1) | Cy3:Cy5(1:1) | Cy3:Cy5(1:1) | Cy3:Cy5(1:1) |
| 9  | Cy3:Cy5(1:1) | Cy3:Cy5(1:1) | Cy3:Cy5(1:1) | Cy3:Cy5(1:1) | Cy3:Cy5(1:1) | Cy3:Cy5(1:1) |
| 10 | Cy3:Cy5(1:1) | Cy3:Cy5(1:1) | Cy3:Cy5(1:1) | Cy3:Cy5(1:1) | Cy3:Cy5(1:1) | Cy3:Cy5(1:1) |
| 11 | Cy3:Cy5(1:1) | Cy3:Cy5(1:1) | Cy3:Cy5(1:1) | Cy3:Cy5(1:1) | Cy3:Cy5(1:1) | Cy3:Cy5(1:1) |
| 12 | Cy3:Cy5(1:1) | Cy3:Cy5(1:1) | Cy3:Cy5(1:1) | Cy3:Cy5(1:1) | Cy3:Cy5(1:1) | Cy3:Cy5(1:1) |
| 13 | Cy3:Cy5(1:1) | Cy3:Cy5(1:1) | Cy3:Cy5(1:1) | Cy3:Cy5(1:1) | Cy3:Cy5(1:1) | Cy3:Cy5(1:1) |
| 14 | Cy3:Cy5(1:1) | Cy3:Cy5(1:1) | Cy3:Cy5(1:1) | Cy3:Cy5(1:1) | Cy3:Cy5(1:1) | Cy3:Cy5(1:1) |
| 15 | Cy3:Cy5(1:1) | Cy3:Cy5(1:1) | Cy3:Cy5(1:1) | Cy3:Cy5(1:1) | Cy3:Cy5(1:1) | Cy3:Cy5(1:1) |
| 16 | Cy3:Cy5(1:1) | Cy3:Cy5(1:1) | Cy3:Cy5(1:1) | Cy3:Cy5(1:1) | Cy3:Cy5(1:1) | Cy3:Cy5(1:1) |
| 17 | Cy3:Cy5(1:1) | Cy3:Cy5(1:1) | Cy3:Cy5(1:1) | Cy3:Cy5(1:1) | Cy3:Cy5(1:1) | Cy3:Cy5(1:1) |
| 18 | Cy3:Cy5(1:1) | Cy3:Cy5(1:1) | Cy3:Cy5(1:1) | Cy3:Cy5(1:1) | Cy3:Cy5(1:1) | Cy3:Cy5(1:1) |

|    | 7 | 8 | 9 | 10 | 10 |
|----|---|---|---|----|----|
| 1  | Cy3:Cy5(1:1) | Cy3:Cy5(1:1) | Cy3:Cy5(1:1) | Cy3:Cy5(1:1) | Cy3:Cy5(1:1) |
| 2  | Cy3:Cy5(1:1) | Cy3:Cy5(1:1) | Cy3:Cy5(1:1) | Cy3:Cy5(1:1) | Cy3:Cy5(1:1) |
| 3  | Cy3:Cy5(1:1) | Cy3:Cy5(1:1) | Cy3:Cy5(1:1) | Cy3:Cy5(1:1) | Cy3:Cy5(1:1) |
| 4  | Cy3:Cy5(1:1) | Cy3:Cy5(1:1) | Cy3:Cy5(1:1) | Cy3:Cy5(1:1) | Cy3:Cy5(1:1) |
| 5  | Cy3:Cy5(1:1) | Cy3:Cy5(1:1) | Cy3:Cy5(1:1) | Cy3:Cy5(1:1) | Cy3:Cy5(1:1) |
| 6  | Cy3:Cy5(1:1) | Cy3:Cy5(1:1) | Cy3:Cy5(1:1) | Cy3:Cy5(1:1) | Cy3:Cy5(1:1) |
| 7  | Cy3:Cy5(1:1) | Cy3:Cy5(1:1) | Cy3:Cy5(1:1) | Cy3:Cy5(1:1) | Cy3:Cy5(1:1) |
| 8  | Cy3:Cy5(1:1) | Cy3:Cy5(1:1) | Cy3:Cy5(1:1) | Cy3:Cy5(1:1) | Cy3:Cy5(1:1) |
| 9  | Cy3:Cy5(1:1) | Cy3:Cy5(1:1) | Cy3:Cy5(1:1) | Cy3:Cy5(1:1) | Cy3:Cy5(1:1) |
| 10 | Cy3:Cy5(1:1) | Cy3:Cy5(1:1) | Cy3:Cy5(1:1) | Cy3:Cy5(1:1) | Cy3:Cy5(1:1) |

-continued

Assembly Map

| | | | | | |
|---|---|---|---|---|---|
| 11 | Cy3:Cy5(1:1) | Cy3:Cy5(1:1) | Cy3:Cy5(1:1) | Cy3:Cy5(1:1) | Cy3:Cy5(1:1) |
| 12 | Cy3:Cy5(1:1) | Cy3:Cy5(1:1) | Cy3:Cy5(1:1) | Cy3:Cy5(1:1) | Cy3:Cy5(1:1) |
| 13 | Cy3:Cy5(1:1) | Cy3:Cy5(1:1) | Cy3:Cy5(1:1) | Cy3:Cy5(1:1) | Cy3:Cy5(1:1) |
| 14 | Cy3:Cy5(1:1) | Cy3:Cy5(1:1) | Cy3:Cy5(1:1) | Cy3:Cy5(1:1) | Cy3:Cy5(1:1) |
| 15 | Cy3:Cy5(1:1) | Cy3:Cy5(1:1) | Cy3:Cy5(1:1) | Cy3:Cy5(1:1) | Cy3:Cy5(1:1) |
| 16 | Cy3:Cy5(1:1) | Cy3:Cy5(1:1) | Cy3:Cy5(1:1) | Cy3:Cy5(1:1) | Cy3:Cy5(1:1) |
| 17 | Cy3:Cy5(1:1) | Cy3:Cy5(1:1) | Cy3:Cy5(1:1) | Cy3:Cy5(1:1) | Cy3:Cy5(1:1) |
| 18 | Cy3:Cy5(1:1) | Cy3:Cy5(1:1) | Cy3:Cy5(1:1) | Cy3:Cy5(1:1) | Cy3:Cy5(1:1) |

A GenePix 4000B with the following settings was used for analysis: 100% Laser power for both colors, gain of 500 for the red channel and gain of 375 for the green channel photomultiplier tube voltage setting, 5 μm resolution, and 175 μm diameter circles. Integrated intensities were calculated for each spot using the GenePix software, and relative standard deviations (RSD) were calculated for all 198 Cy5 spots, 198 Cy3 spots and the ratio of Cy3/Cy5 spots. As seen in Table 1, the coefficient of variation (CV) is lower for all 10 slides when using a ratio of the Cy3/Cy5 integrated intensity compared to the intensity of the Cy3 or Cy5 signals, in some cases by a factor as high as 3. This data support the implementation of an internal fluorescence control, such as a Cy5 dye, that is scanned or imaged as part of the manufacturing QC to compensate for variability due to UV dosage, temperature, surface properties, synthesis, viscosity, condensation, washing (i.e., due to effects caused by differences in temperature, viscosity, flow rate, stringency or anything that may influence the removal or distortion of the spots), depth of pin immersion in the polymer solution for pin printing technologies or any property that could influence the morphology and or concentration of the probes within a given spot.

in compensating for the variability in the intensity of fluorescence. Table 2 shows the fluorescence data of one set of 4 gel drops in MRSA microarrays doped with Cy5 fluorophores and MecA probes. Integral signal intensities were tabulated for all 4 replicate drops taken during factory QC (red-channel) and post-hybridization (green-channel). Due to physical damage to replicate 3, both the red-channel and green-channel showed significantly reduced integral signal intensities for replicate 3. As the result of the reduced replicate 3, signal intensity, the relative deviation is 23.8% and 29.5% for red-channel and green-channels, respectively. When the green-channel and red-channel data is calculated as a ratio, the relative deviation is reduced to 12.2%. This demonstrates that internal fluorescence control data (red-channel) can be used to reduce the variability of the microarray image and/or microarray production.

TABLE 2

Integral of Signal Intensities

| | Replicate 1 | Replicate 2 | Replicate 3 | Replicate 4 | Mean | Standard Deviation | % RSD |
|---|---|---|---|---|---|---|---|
| Red-Channel | 1031897 | 1095959 | 613676 | 1063218 | 951187 | 226522 | 23.8% |
| Green-Channel | 2812769 | 3707689 | 1909522 | 3874995 | 3076244 | 906896 | 29.5% |
| Green/Red Ratio | 2.725823 | 3.383054 | 3.111613 | 3.644591 | 3.21627 | 0.392754 | 12.2% |

TABLE 1

| Slide | Cy5 RSD | Cy3 RSD | Cy3/Cy5 RSD |
|---|---|---|---|
| 1 | 17.5% | 12.1% | 7.6% |
| 2 | 14.3% | 10.0% | 5.5% |
| 3 | 10.8% | 8.5% | 3.1% |
| 4 | 5.5% | 3.7% | 3.0% |
| 5 | 7.5% | 6.0% | 2.5% |
| 6 | 5.1% | 5.0% | 1.4% |
| 7 | 8.5% | 6.0% | 4.1% |
| 8 | 11.7% | 7.8% | 5.1% |
| 9 | 6.6% | 5.0% | 3.6% |
| 10 | 4.6% | 4.5% | 3.5% |

Example 2

Method of Image Analysis

The internal fluorescence control has been implemented on Akonni's MRSA microarrays and shown to be effective Example 3

Algorithms for Image Generation
Algorithm 1
This algorithm takes a pre-hybridization Cy5 QC image of the array and generates a data file containing QC parameters of the array.
1. Read the Cy5 QC image and create two local copies, one is the un-altered original (CY5_Original), and another one will be transformed into a binary image (Cy5_Processed) in steps 2 and 3.
2. Take the Cy5_Processed image, apply digital filtering and pixel operation to produce an image with uniform and zero-valued background.
3. Threshold the image into a binary image and save as Cy5_Processed.
4. Apply particle analysis to the binary image (Cy5_Processed) to identified, filtered objects based on size. Measure and record parameters of the objects: center of mass, bounding box, particle area and ellipticity.
5. Check to see if the number of objects identified in step 4 meets minimum requirement, otherwise reject the slide.
6. Find grid.
    a. Select one object and assume its center of mass is the grid origin.
    b. Form the grid and calculate the pixel location of each grid cell.

c. Apply all objects to the grid and check if at least 80% of the grid cell that should contain a Cy3 drop, has objects inside. If yes, the grid has been found and proceed to step 7. If not, repeat 6A through 6C with a different object's center of mass as the grid origin.
7. Rotate the image so the angle formed by the Cy3 drops is less than 0.2 degree from the horizontal axis.
8. Fine-tune the grid. Because in step 6, grid origin is determined by center of mass from an object in the binary image, the center of mass could deviate slightly from the true center of the object.
   a. Move the grid origin by (0,1), i.e, subtract X-coordinate by 0 pixel and Y-coordinate by 1 pixel.
   b. For each Cy3 drop, calculate the following:
      i. Deviation X: Distance in X coordinate between center of Cy3 drop and center of its grid cell.
      ii. Deviation Y: Distance in Y coordinates between center of Cy3 drop and center of its grid cell.
   c. Summarize the deviations for all Cy3 drops, using score=Sum(abs(DeviationX)+abs(DeviationY)). A lower score means better grid placement.
   d. Repeat 8A through 8C for a total of 24 combinations, shown in the table below.
   e.

| | | | | |
|---|---|---|---|---|
| −2, 2 | −1, 2 | 0, 2 | 1, 2 | 2, 2 |
| −2, 1 | −1, 1 | 0, 1 | 1, 1 | 2, 1 |
| −2, 0 | −1, 0 | | −1, 0 | 2, 0 |
| −2, −1 | −1, −1 | 0, −1 | 1, −1 | 2, −1 |
| −2, −2 | −1, −2 | 0, −2 | 1, −2 | 2, −2 | f. Choose the grid center so its score is the lowest.
9. Calculate QC data of each spot.
   a. Deviation X: X coordinate of center of drop MINUS X coordinate of center of grid cell.
   b. Deviation Y: Y coordinate of center of drop MINUS Y coordinate of center of grid cell.
   c. Reject Flag: Reject a spot based on diameter, ellipticity, etc.
   d. Spot Intensity
   e. Diameter
10. Write QC data to a text file, refer to Table 3.

TABLE 3

Example Array QC Data.

| Grid Row | Grid Column | Spot Type | Reject? | Grid Center X | Grid Center Y | Deviation X | Deviation Y | Spot Intensity | Diameter |
|---|---|---|---|---|---|---|---|---|---|
| 1 | 1 | Cy3 | FALSE | 105 | 88 | 3 | 1 | 2143818 | 8.85 |
| 1 | 2 | Empty | FALSE | 135 | 88 | 0 | 0 | 261 | 0.00 |
| 1 | 3 | Empty | FALSE | 166 | 88 | 0 | 0 | 568 | 0.00 |
| 1 | 4 | Empty | FALSE | 196 | 88 | 0 | 0 | −87 | 0.00 |
| 1 | 5 | Empty | FALSE | 226 | 88 | 0 | 0 | 228 | 0.00 |
| 1 | 6 | Cy3 | FALSE | 257 | 88 | 0 | 3 | 1612600 | 9.72 |
| 1 | 7 | Cy3 | FALSE | 287 | 88 | 1 | 3 | 1567664 | 9.02 |
| 1 | 8 | Empty | FALSE | 318 | 88 | 0 | 0 | 506 | 0.00 |
| 1 | 9 | Empty | FALSE | 348 | 88 | 0 | 0 | 1426 | 0.00 |
| 1 | 10 | Empty | FALSE | 378 | 88 | 0 | 0 | 3420 | 0.00 |
| 1 | 11 | Empty | FALSE | 409 | 88 | 0 | 0 | 991 | 0.00 |
| 1 | 12 | Cy3 | FALSE | 439 | 88 | −1 | 3 | 2216029 | 9.65 |
| 2 | 1 | Empty | FALSE | 105 | 119 | 0 | 0 | −319 | 0.00 |
| 2 | 2 | Empty | FALSE | 135 | 119 | 0 | 0 | 334 | 0.00 |
| 2 | 3 | Probe 31 | FALSE | 166 | 119 | 5 | 0 | 1618379 | 10.12 |
| 2 | 4 | Empty | FALSE | 196 | 119 | 0 | 0 | 486 | 0.00 |
| 2 | 5 | Empty | FALSE | 226 | 119 | 0 | 0 | 83 | 0.00 |
| 2 | 6 | H | FALSE | 257 | 119 | −1 | −1 | 1750396 | 8.99 |
| 2 | 7 | Empty | FALSE | 287 | 119 | 0 | 0 | 40709 | 0.00 |
| 2 | 8 | Empty | FALSE | 318 | 119 | 0 | 0 | −162 | 0.00 |
| 2 | 9 | Probe 31 | FALSE | 348 | 119 | 0 | 3 | 2061064 | 10.61 |
| 2 | 10 | Empty | FALSE | 378 | 119 | 0 | 0 | 127 | 0.00 |
| 2 | 11 | Empty | FALSE | 409 | 119 | 0 | 0 | 289 | 0.00 |
| 2 | 12 | H | FALSE | 439 | 119 | −1 | 3 | 2030635 | 9.19 |
| 3 | 1 | Empty | FALSE | 105 | 149 | 0 | 0 | 1143 | 0.00 |
| 3 | 2 | Probe 14 | FALSE | 135 | 149 | 4 | 1 | 2222565 | 9.43 |
| 3 | 3 | Probe 35 | FALSE | 166 | 149 | 2 | 1 | 2088478 | 9.16 |
| 3 | 4 | Empty | FALSE | 196 | 149 | 0 | 0 | 3938 | 0.00 |
| 3 | 5 | Empty | FALSE | 226 | 149 | 0 | 0 | −96 | 0.00 |
| 3 | 6 | Empty | FALSE | 257 | 149 | 0 | 0 | −33 | 0.00 |
| 3 | 7 | Empty | FALSE | 287 | 149 | 0 | 0 | 582 | 0.00 |
| 3 | 8 | Probe 14 | FALSE | 318 | 149 | 0 | 1 | 2073261 | 9.90 |
| 3 | 9 | Probe 35 | FALSE | 348 | 149 | 2 | 1 | 1651170 | 8.86 |
| 3 | 10 | Empty | FALSE | 378 | 149 | 0 | 0 | 837 | 0.00 |
| 3 | 11 | Empty | FALSE | 409 | 149 | 0 | 0 | 370 | 0.00 |
| 3 | 12 | Empty | FALSE | 439 | 149 | 0 | 0 | 315 | 0.00 |
| 4 | 1 | Empty | FALSE | 105 | 180 | 0 | 0 | 162 | 0.00 |
| 4 | 2 | Empty | FALSE | 135 | 180 | 0 | 0 | −179 | 0.00 |
| 4 | 3 | Probe 36 | FALSE | 166 | 180 | 3 | 2 | 1782715 | 8.49 |
| 4 | 4 | Empty | FALSE | 196 | 180 | 0 | 0 | 633 | 0.00 |
| 4 | 5 | Probe 29 | FALSE | 226 | 180 | 3 | 0 | 1715205 | 9.51 |
| 4 | 6 | Empty | FALSE | 257 | 180 | 0 | 0 | 274 | 0.00 |
| 4 | 7 | Empty | FALSE | 287 | 180 | 0 | 0 | 242 | 0.00 |
| 4 | 8 | Empty | FALSE | 318 | 180 | 0 | 0 | 329 | 0.00 |
| 4 | 9 | Probe 36 | FALSE | 348 | 180 | −1 | −1 | 1666545 | 9.66 |
| 4 | 10 | Empty | FALSE | 378 | 180 | 0 | 0 | 12157 | 0.00 |
| 4 | 11 | Probe 29 | FALSE | 409 | 180 | −1 | 1 | 1706590 | 10.47 |

TABLE 3-continued

Example Array QC Data.

| Grid Row | Grid Column | Spot Type | Reject? | Grid Center X | Grid Center Y | Deviation X | Deviation Y | Spot Intensity | Diameter |
|---|---|---|---|---|---|---|---|---|---|
| 4 | 12 | Empty | FALSE | 439 | 180 | 0 | 0 | 1180 | 0.00 |
| 5 | 1 | Empty | FALSE | 105 | 210 | 0 | 0 | 308 | 0.00 |
| 5 | 2 | Empty | FALSE | 135 | 210 | 0 | 0 | 180 | 0.00 |
| 5 | 3 | Probe 37 | FALSE | 166 | 210 | 2 | 1 | 1537455 | 9.70 |
| 5 | 4 | dN20 | FALSE | 196 | 210 | 1 | 0 | 1854849 | 10.35 |
| 5 | 5 | Empty | FALSE | 226 | 210 | 0 | 0 | 486 | 0.00 |
| 5 | 6 | Probe 90 | FALSE | 257 | 210 | 2 | 1 | 1697651 | 9.01 |
| 5 | 7 | Empty | FALSE | 287 | 210 | 0 | 0 | −115 | 0.00 |
| 5 | 8 | Empty | FALSE | 318 | 210 | 0 | 0 | −382 | 0.00 |
| 5 | 9 | Probe 37 | FALSE | 348 | 210 | 1 | 2 | 2009715 | 9.84 |
| 5 | 10 | dN20 | FALSE | 378 | 210 | 0 | 1 | 2187695 | 10.80 |
| 5 | 11 | Empty | FALSE | 409 | 210 | 0 | 0 | 1099 | 0.00 |
| 5 | 12 | Probe 90 | FALSE | 439 | 210 | 0 | 0 | 2007504 | 10.03 |
| 6 | 1 | Cy3 | FALSE | 105 | 240 | 5 | 0 | 1264671 | 8.35 |
| 6 | 2 | Empty | FALSE | 135 | 240 | 0 | 0 | −203 | 0.00 |
| 6 | 3 | Empty | FALSE | 166 | 240 | 0 | 0 | 476 | 0.00 |
| 6 | 4 | Empty | FALSE | 196 | 240 | 0 | 0 | 214 | 0.00 |
| 6 | 5 | Empty | FALSE | 226 | 240 | 0 | 0 | 695 | 0.00 |
| 6 | 6 | Empty | FALSE | 257 | 240 | 0 | 0 | 218 | 0.00 |
| 6 | 7 | Cy3 | FALSE | 287 | 240 | 1 | 3 | 1125959 | 9.57 |
| 6 | 8 | Empty | FALSE | 318 | 240 | 0 | 0 | 107 | 0.00 |
| 6 | 9 | Empty | FALSE | 348 | 240 | 0 | 0 | 874 | 0.00 |
| 6 | 10 | Empty | FALSE | 378 | 240 | 0 | 0 | 617 | 0.00 |
| 6 | 11 | Empty | FALSE | 409 | 240 | 0 | 0 | 528 | 0.00 |
| 6 | 12 | Empty | FALSE | 439 | 240 | 0 | 0 | 580 | 0.00 |
| 7 | 1 | Cy3 | FALSE | 105 | 271 | 1 | −1 | 1734877 | 9.71 |
| 7 | 2 | Empty | FALSE | 135 | 271 | 0 | 0 | −634 | 0.00 |
| 7 | 3 | Empty | FALSE | 166 | 271 | 0 | 0 | −69 | 0.00 |
| 7 | 4 | Empty | FALSE | 196 | 271 | 0 | 0 | 276 | 0.00 |
| 7 | 5 | Empty | FALSE | 226 | 271 | 0 | 0 | −199 | 0.00 |
| 7 | 6 | Cy3 | FALSE | 257 | 271 | 0 | −2 | 1581737 | 10.49 |
| 7 | 7 | Cy3 | FALSE | 287 | 271 | 0 | 0 | 1522026 | 9.37 |
| 7 | 8 | Empty | FALSE | 318 | 271 | 0 | 0 | −748 | 0.00 |
| 7 | 9 | Empty | FALSE | 348 | 271 | 0 | 0 | 2635 | 0.00 |
| 7 | 10 | Empty | FALSE | 378 | 271 | 0 | 0 | 747 | 0.00 |
| 7 | 11 | Empty | FALSE | 409 | 271 | 0 | 0 | 246 | 0.00 |
| 7 | 12 | Cy3 | FALSE | 439 | 271 | −1 | 0 | 1640104 | 10.37 |
| 8 | 1 | Empty | FALSE | 105 | 301 | 0 | 0 | 586 | 0.00 |
| 8 | 2 | Empty | FALSE | 135 | 301 | 0 | 0 | 439 | 0.00 |
| 8 | 3 | Probe 31 | FALSE | 166 | 301 | 1 | −1 | 2008843 | 10.06 |
| 8 | 4 | Empty | FALSE | 196 | 301 | 0 | 0 | 247 | 0.00 |
| 8 | 5 | Empty | FALSE | 226 | 301 | 0 | 0 | 319 | 0.00 |
| 8 | 6 | H | FALSE | 257 | 301 | −1 | 0 | 1534132 | 10.46 |
| 8 | 7 | Empty | FALSE | 287 | 301 | 0 | 0 | −477 | 0.00 |
| 8 | 8 | Empty | FALSE | 318 | 301 | 0 | 0 | 13815 | 0.00 |
| 8 | 9 | Probe 31 | FALSE | 348 | 301 | −1 | −1 | 1704828 | 10.04 |
| 8 | 10 | Empty | FALSE | 378 | 301 | 0 | 0 | 260 | 0.00 |
| 8 | 11 | Empty | FALSE | 409 | 301 | 0 | 0 | 2993 | 0.00 |
| 8 | 12 | H | FALSE | 439 | 301 | 0 | 2 | 1569671 | 9.96 |
| 9 | 1 | Empty | FALSE | 105 | 332 | 0 | 0 | 148 | 0.00 |
| 9 | 2 | Probe 14 | FALSE | 135 | 332 | 2 | −3 | 1969286 | 9.77 |
| 9 | 3 | Probe 35 | FALSE | 166 | 332 | 3 | −1 | 1636381 | 9.53 |
| 9 | 4 | Empty | FALSE | 196 | 332 | 0 | 0 | 792 | 0.00 |
| 9 | 5 | Empty | FALSE | 226 | 332 | 0 | 0 | −377 | 0.00 |
| 9 | 6 | Empty | FALSE | 257 | 332 | 0 | 0 | 594 | 0.00 |
| 9 | 7 | Empty | FALSE | 287 | 332 | 0 | 0 | 570 | 0.00 |
| 9 | 8 | Probe 14 | FALSE | 318 | 332 | 1 | −3 | 1812677 | 10.36 |
| 9 | 9 | Probe 35 | FALSE | 348 | 332 | 0 | −2 | 1881764 | 9.97 |
| 9 | 10 | Empty | FALSE | 378 | 332 | 0 | 0 | 444 | 0.00 |
| 9 | 11 | Empty | FALSE | 409 | 332 | 0 | 0 | −423 | 0.00 |
| 9 | 12 | Empty | FALSE | 439 | 332 | 0 | 0 | 287 | 0.00 |
| 10 | 1 | Empty | FALSE | 105 | 362 | 0 | 0 | 426 | 0.00 |
| 10 | 2 | Empty | FALSE | 135 | 362 | 0 | 0 | −23 | 0.00 |
| 10 | 3 | Probe 36 | FALSE | 166 | 362 | 1 | −4 | 1582212 | 9.85 |
| 10 | 4 | Empty | FALSE | 196 | 362 | 0 | 0 | 1518 | 0.00 |
| 10 | 5 | Probe 29 | FALSE | 226 | 362 | 1 | −1 | 1629291 | 11.09 |
| 10 | 6 | Empty | FALSE | 257 | 362 | 0 | 0 | 4511 | 0.00 |
| 10 | 7 | Empty | FALSE | 287 | 362 | 0 | 0 | 201 | 0.00 |
| 10 | 8 | Empty | FALSE | 318 | 362 | 0 | 0 | −397 | 0.00 |
| 10 | 9 | Probe 36 | FALSE | 348 | 362 | −1 | 1 | 1683589 | 9.69 |
| 10 | 10 | Empty | FALSE | 378 | 362 | 0 | 0 | 75 | 0.00 |
| 10 | 11 | Probe 29 | FALSE | 409 | 362 | 0 | 1 | 1763951 | 10.31 |
| 10 | 12 | Empty | FALSE | 439 | 362 | 0 | 0 | 607 | 0.00 |
| 11 | 1 | Empty | FALSE | 105 | 392 | 0 | 0 | −321 | 0.00 |
| 11 | 2 | Empty | FALSE | 135 | 392 | 0 | 0 | 437 | 0.00 |

TABLE 3-continued

Example Array QC Data.

| Grid Row | Grid Column | Spot Type | Reject? | Grid Center X | Grid Center Y | Deviation X | Deviation Y | Spot Intensity | Diameter |
|---|---|---|---|---|---|---|---|---|---|
| 11 | 3 | Probe 37 | FALSE | 166 | 392 | 0 | −4 | 1782130 | 9.95 |
| 11 | 4 | dN20 | FALSE | 196 | 392 | 3 | −2 | 1886735 | 10.28 |
| 11 | 5 | Empty | FALSE | 226 | 392 | 0 | 0 | 293 | 0.00 |
| 11 | 6 | Probe 90 | FALSE | 257 | 392 | 0 | −4 | 1569567 | 10.77 |
| 11 | 7 | Empty | FALSE | 287 | 392 | 0 | 0 | 1805 | 0.00 |
| 11 | 8 | Empty | FALSE | 318 | 392 | 0 | 0 | −262 | 0.00 |
| 11 | 9 | Probe 37 | FALSE | 348 | 392 | −1 | −3 | 1872819 | 9.83 |
| 11 | 10 | dN20 | FALSE | 378 | 392 | 1 | −4 | 2034194 | 10.21 |
| 11 | 11 | Empty | FALSE | 409 | 392 | 0 | 0 | −258 | 0.00 |
| 11 | 12 | Probe 90 | FALSE | 439 | 392 | 0 | 0 | 1693534 | 10.95 |
| 12 | 1 | Cy3 | FALSE | 105 | 423 | 3 | −1 | 1658433 | 8.06 |
| 12 | 2 | Empty | FALSE | 135 | 423 | 0 | 0 | 521 | 0.00 |
| 12 | 3 | Empty | FALSE | 166 | 423 | 0 | 0 | 285 | 0.00 |
| 12 | 4 | Empty | FALSE | 196 | 423 | 0 | 0 | −447 | 0.00 |
| 12 | 5 | Empty | FALSE | 226 | 423 | 0 | 0 | −436 | 0.00 |
| 12 | 6 | Empty | FALSE | 257 | 423 | 0 | 0 | −129 | 0.00 |
| 12 | 1 | Cy3 | FALSE | 287 | 423 | 1 | 0 | 1392853 | 8.72 |
| 12 | 8 | Empty | FALSE | 318 | 423 | 0 | 0 | 257 | 0.00 |
| 12 | 9 | Empty | FALSE | 348 | 423 | 0 | 0 | 649 | 0.00 |
| 12 | 10 | Empty | FALSE | 378 | 423 | 0 | 0 | −108 | 0.00 |
| 12 | 11 | Empty | FALSE | 409 | 423 | 0 | 0 | 64 | 0.00 |
| 12 | 12 | Empty | FALSE | 439 | 423 | 0 | 0 | −84 | 0.00 |

Algorithm 2

This process takes two pictures of the post-hybridization array: one with normal exposure (Image_NormalExposure) and one with high-exposure to emphasize the Cy3 beacon (Image_HighExposure).
1. Read Image_HighExposure and Image_NormalExposure into memory.
2. Read from QC text file.
3. Operate on Image_HighExposure Image to find grid.
a. Take the Cy5_HighExposure image, apply digital filtering and pixel operation to produce an image with uniform and zero-valued background.
b. Threshold the image to into a binary image.
c. Apply particle analysis to the binary image to identified, filtered objects based on size. Measure and record parameters of the objects: center of mass, bounding box, particle area and ellipticity.
d. Check to see if the number of objects identified in step 3C meets the minimum requirement, otherwise reject the slide.
e. Find grid, similar to step 6 in Algorithm 1.
f. Rotate the image so the angle formed by the Cy3 drops is less than 0.2 degree from the horizontal axis.
g. Fine-tune the grid, similar to step 8 in Algorithm 1.
4. Apply the grid found in Image_HighExposure to the Image_NormalExposure.
5. Using X-Deviation, Y-Deviation, diameter and reject flag from the QC file to determine the relevant spot parameters.
a. If Reject Flag is true, then exclude the spot from analysis.
b. Spot X coordinate: X coordinate of the center of the grid PLUS X-Deviation.
c. Spot X coordinate: Y coordinate of the center of the grid PLUS Y-Deviation.
d. Spot diameter: Spot diameter from QC data.
6. Calculate intensity of spot and background.
7. Perform final calculation to determine analytical results.

Example 4

A protein microarray assembly is constructed using gel drop elements containing antibodies. Glass slides with printed gel element microarrays are blocked with PBS containing 1% BSA for 1 hour at room temperature. The slides are rinsed with DI water and allowed to air dry in a dust-free environment. The microarray assembly is then assembled with the blocked glass slide, laser cut 256M tape from Adchem, hydrophilic Lexan film, and a reservoir. Approximately 0.5 mL of SEB (1 μg/mL in PBS with 0.05% Tween-20 and 1% BSA) is pipetted into the reservoir of the microarray system, and continuously imbibes through the array chamber at room temperature. Next, 0.2 mL of anti-SEB monoclonal antibody dilution in PBST with 1% BSA is pipetted into the reservoir of the microarray system, which continuously imbibes through the array chamber and into the waste chamber. Then, 0.2 mL of PBST is pipetted into the reservoir of the microarray system, which continuously imbibes through the array chamber and into the absorbent of the waste chamber. Subsequently, 0.1 mL of Alexa 568 labeled anti-mouse antibody at 2 μg/mL in PBST with 1% BSA is pipetted into the reservoir of the microarray system, which continuously imbibes through the array chamber and into the absorbent of the waste chamber. An additional 0.2 mL of PBST wash is pipetted into the reservoir of the microarray system, which continuously imbibes through the array chamber and into the absorbent of the waste chamber. The microarray system is then imaged using a green laser (532 nm) with 605 nm filter on Aurora PortArray 5000.

Example 5

Figure 9:
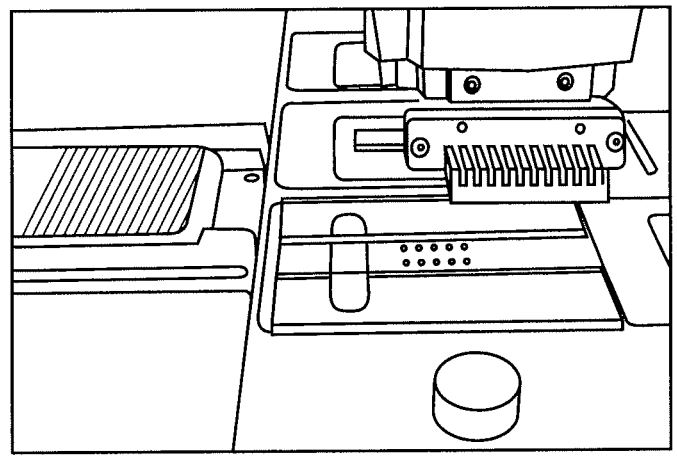
FIG. 9 shows a picture of a thin-film vacuum manifold for blunt pin printing.

Oligonucleotide mixtures are synthesized for MRSA according to the array map shown in FIG. 9. Each probe is synthesized along with the internal control probe Cy5. Additional Cy3 control probes, attached to the same oligonucleotide sequence, are also mixed with the Cy5 control probes. Cy3/Cy5 spots are printed in concentrations that range from 0.1 nM to 10 μM in 1 log concentration changes for the purposes of establishing a calibration curve. An imaging system consists of two optical trains. Both optical trains consist of an LED and a non-cooled CCD camera. One optical train is for detecting Cy3 spots (550 nm excitation and 570 nm emission), and the other optical train is for detecting Cy5 spots (650 nm excitation and 670 nm emission). The optical trains are fixed in space in relation to the instrument. A moving stage moves the array to the green channel and 10 images are acquired to improve the dynamic range; acquisition of multiple images at short exposure times prevents saturation that may occur as a result of using materials with high autofluorescence while also allowing signal averaging to reduce the effect of random noise. The stage moves the array to the red channel and 10 images are acquired. The process repeats 5 times to account for possible misalignment due to positional accuracies, improper exposure time, out of focus spots and/or any other anomalies that might compromise proper imaging. A calibration curve is plotted with respect to the Cy3/Cy5 serial dilution of concentrations as shown by the outer boundary of the array in the assembly map below. The calibration curve, derived from this concentration gradient, is intended to correct for factors that affect the entire assembly such as shelf-life degradation of the probes, temperature, changes in UV dosage, synthesis variations, or any systemic artifact that can result in irreproducible behavior. The calibration curve for Cy5 is plotted during analysis with the calibration curve for Cy3.

$$I_{red} = m_{red} \times \text{moles}(Cy5) + b_{red}$$

$$I_{green} = m_{green} \times \text{moles}(Cy3) + b_{green}$$

where $I_{red}$ and $I_{green}$ are background-subtracted integral intensities. The slopes, $m_{red}$ and $m_{green}$, and the intercepts, $b_{red}$ and $b_{green}$, are calculated from these calibration curves. Averages of the calibration curves are plotted and outliers are rejected. To account for irreproducibility from spot-to-spot, assembly-to-assembly and lot-to-lot, the Cy5 background-subtracted integral intensity value is calculated for each spot. During synthesis, the probe (14, 31, 35, 36, 37, 29, 90, H, or dN20) concentrations for each spot have an equimolar concentration of oligonucleotide probe and Cy5 fluorophores for each spot. Thus, the following relationship holds:

Cy3 concentration≈Cy5 concentration.

Therefore, $$I_{green,saturation} \approx m_{green} \times \text{moles}(Cy5) + b_{green}$$

where $I_{green,saturation}$ represents the hypothetical situation where all probes in the gel element are bound to labeled-Cy3 molecules. Note, moles(Cy5) replaces moles(Cy3) because of equimolar equivalency in the equation above. The background-corrected integral intensity of the probes for spots that determine presence of MRSA is measured at the representative spots, and calculated. If this intensity meets the following criteria:

$$\frac{I_{green,meas}}{I_{green,saturation}} > 0.001$$

the value is considered positive. That is, more than 0.1% of the possible probe molecules have bound target with Cy3 labels. This method may also be used for quantitation.

Example 6

Kiss-cut tape reels are manufactured for the spacer tape reel, which contains the spacer cut out, and the cover tape reel are pre-punched with the inlet and vent fill holes. As shown in FIG. 5, during production, the substrate film reel unravels and the release liner is collected on the top reel. The gel element printer prints the gel elements on the substrate film. The film is then exposed to UV under an inert atmosphere (e.g., Argon gas). Positive pressure of Argon is slowly added to the Argon chamber, and since its density is greater than air, it settles to the bottom of the chamber where the substrate is. This allows for a low flow rate of Argon into the chamber, and thus requires minimal demand on room make-up air. To ensure that no unpolymerized polymer is left on the substrate, the substrate travels through a wash station, which is positioned in such a way as to eliminate any splash into the polymerization chamber. The washed arrays are dried with a conventional air knife assembly. A QC camera ensures that that the elements are printed within specification and a rejection marker alerts the operator to discard assemblies out of specification. The double-sided spacer tape, which defines the microarray chamber, is unraveled and bonded to the substrate. The openings in the spacer tape are designed to allow for fairly loose tolerances during the lamination of the spacer tape to the substrate, which allows the manufacture of gel element arrays of variable geometry and complexity without modifying the assembly line. A rollable absorbent is unwound and mounted to the waste chamber of the assembly where it is sealed in place with either an adhesive or double-sided tape. An alternative strategy for including the absorbent is to use a pick-and-place robot to insert the absorbent into a waste chamber. The current flow cell design uses an additional spacer layer to accommodate an absorbent that is twice as thick as the reaction chamber. Finally, the cover film, which has fill holes, is applied. The fill holes can be considerably larger or smaller than the holes in the spacer allowing for loose tolerances during alignment. A guillotine then cuts the tape into the appropriate size.

Pin-printing robots typically feature a print head that is populated with precisely machined pins. The print head is attached to a precision xyz-axis control arm (FIG. 7). The control arm is responsible for moving the print head with micron-accuracy between the printing solution source plate (e.g., a 384 well microtiter plate), the substrate printing station (the platen), and a wash station (for cleaning the pins between deposition of unique solutions). Alternatively, a high-throughput, non-contact print head deposits multiple solutions simultaneously within the microarray-PCR reaction chamber.

In some embodiments, the entire microarray is printed in a single-stroke. Electrical Discharge Machining (EDM) can be used to create print heads with 125 micron pins (diameter of pins currently used) and the presently-used 300 micron centers. Additionally, Parallel Synthesis Designs offers 24576 well plates, which has wells with 560 micron centers. This translates to approximately 350 spots per square cm. While this many spots is sufficiently adequate for most diagnostic applications, tests that require additional spots can be accommodated by arranging multiple printers serially in the assembly line, increasing printing time only by the travel from one printer to the next. Another embodiment for printing on a moving film includes the use of a non-contact printer, which implements a piezoelectric crystal and a capillary that aspirates the microarray printing solution and dispenses picoliter to nanoliter drops onto the substrate. The printing head may include multiple capillaries for simultaneously printing an array of unique microarrays spots with distinct probes. Furthermore, this print head may be a high density array of capillaries for increasing the number of unique microarray spots. Alternatively, the print head may raster across and up and down the substrate film to print replicate spots or the print head raster method may be used to aspirate a separate polymer-probe suspension for printing multiple unique spots using the same print head. Another option is to have the substrate film re-loaded onto the reel-to-reel system following a first print pass, so as to re-print additional (unique) spots for each microarray on the roll of substrate film. This re-printing approach may include fiducials to properly align the film when printing on the second, third or $n^{th}$ pass. One example of a relevant fiducial is the use of perforated edges, such as those used with 35 mm film. Another printing option includes acoustic ejection, a non-contact method available from Labcyte, in which high frequency sound waves eject nL droplets from a source plate to a destination plate Example 7

Figure 10:
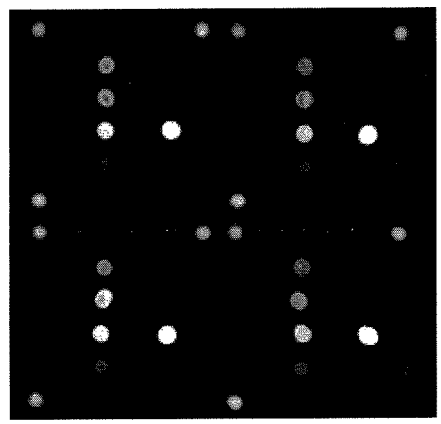

FIG. 8 shows the result of printing Cy3 gel elements on a 0.005" polyester film that was purchased from McMaster-Carr (Santa Fe Springs, Calif.) in a roll format. The film was placed in the vacuum chuck shown in FIG. 9 and printed on. It was imaged using bright field illumination before and after polymerization. This array was also imaged with an Akonni imager that consists of an LED and a non-cooled camera. Subsequent to this printing, an MRSA array, described above, was printed on the polyester film and exposed to a Qiagen MasterMix using 300 pg of purified MRSA DNA. Thermocycling was performed on a Quanta Bioscience slide block thermocycler. The result when using a rollable film for the top and bottom surfaces as well as the spacer tape is shown in FIG. 10, which shows positive identification of MRSA. FIG. 11 shows a reel-to-reel printing setup with a BioDot Ultranon-contact array printer (top panel) and video frames of non-contact printing using the BioDot Ultra on a moving film that has not been chemically treated or modified (bottom panels). These results demonstrate the feasibility of printing, microarrays on a moving film with a non-contact array printer, which allows for high speed and low cost production of microarray assemblies of the present application.

Example 8

Figure 12:
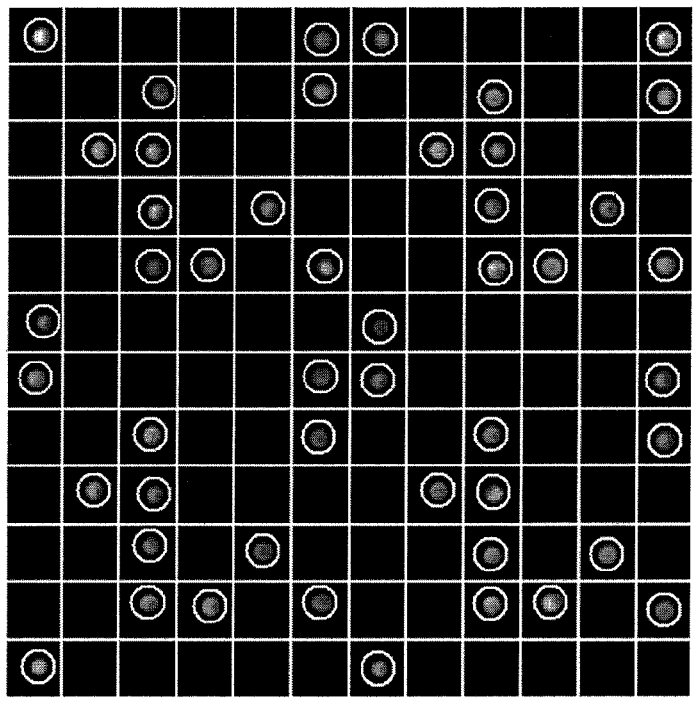
FIG. 12 shows a red channel fluorescence image of the MRSA array captured during factory QC to extract spot parameters.
Figure 13:
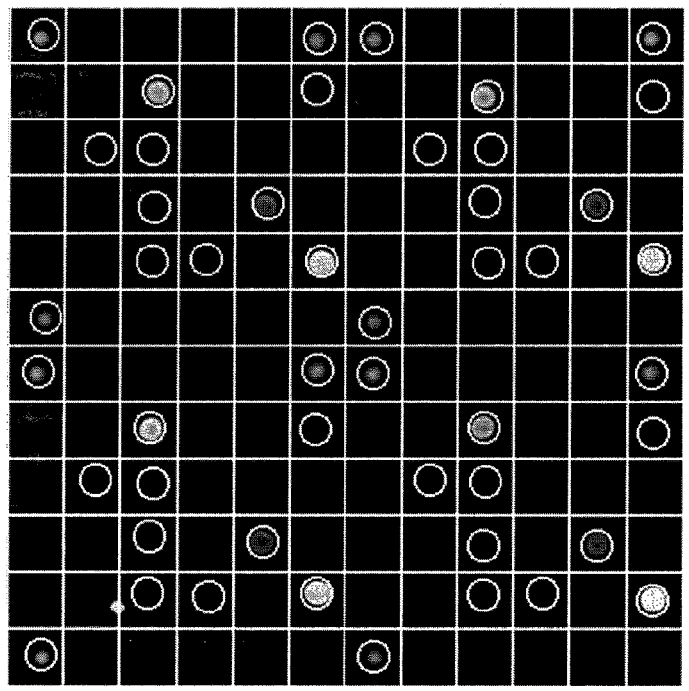
FIG. 13 shows a green channel fluorescence image of hybridized array imaged by end-user's imager. The imager software utilized the array QC data to place the grid and circles around each individual spot.
Figure 14:
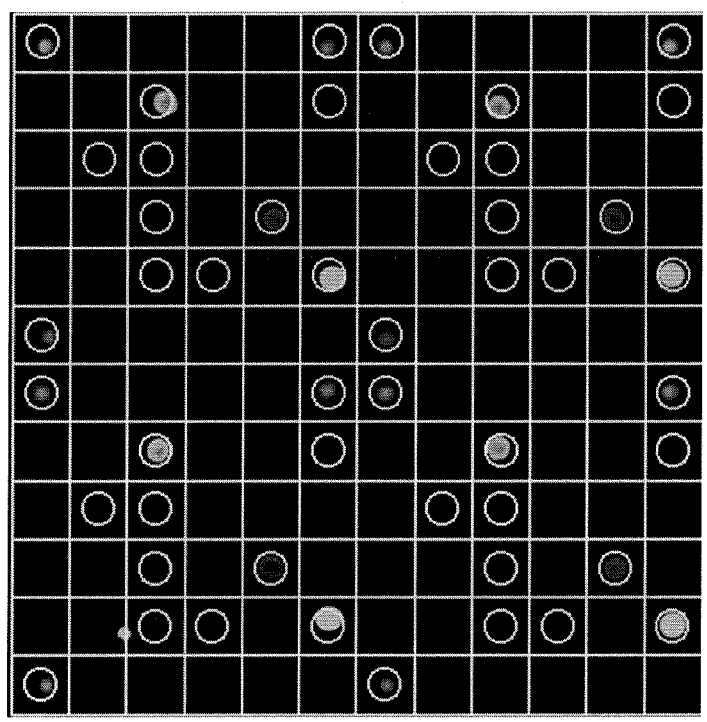
FIG. 14 shows a fluorescence image of hybridized array imaged by end-user equipment without the use of QC data, making it more challenging to place the grid and circles around each individual spot.

FIGS. 12-14 show the array image analysis process. FIG. 12 is an image of an array taken at factory QC with red channel imager to extract array QC data. The QC software algorithm automatically finds each spot in the array and associates each spot to its perspective location in the array grid. The software displays the 12 by 12 square grid and draws circle around each drop. The QC software calculates the relative location (Deviation X, Deviation Y) of each circle within its bounding square grid box and stores the information as part of the QC data to assist in post-hybridization image analysis.

FIG. 13 is an image of the array is taken after hybridization with end-user's green channel imager. The image analysis software locates the array grid based on Cy3 fluorescent beacons and draws the 12 by 12 square grid. The image analysis then use the relative location of the spot (Deviation X and Deviation Y from the array QC file) to locate each spot and draws circle around the spot for visual indication. Note that with the assistance of array QC data, the software was able to locate every spot on the arrays and draw circles that fully enclose each spot.

FIG. 14 is an image of the array is taken after hybridization with end-user's green channel imager. The image analysis software locates the array grid based on Cy3 fluorescent beacons and draws the 12 by 12 square grid. For this image, image analysis software does not have access to information on relative spot location from the array QC file. Instead, the image analysis software identified each spot by assume the center of each square grid cell is the center of the spot. The software has incorrectly identified several spots, by drawing circles that do not fully enclose the spot. The incorrectly identified spots include spots located in: row 2 column 2, row 11 column 6. Note that this method of image analysis without array QC data is less robust in spot identification than image analysis with array QC data shown in FIG. 13.

What is claimed is:

1. A microarray assembly for detection of a target molecule in a sample, comprising:
    an array chamber with a sample inlet, a sample outlet, a top interior surface, a bottom interior surface, side walls and a microarray located on the bottom interior surface, wherein the array chamber is designed to allow amplification of nucleic acids in the array chamber and hybridization of amplified nucleic acid to the microarray and wherein the top interior surface is a hydrophilic surface that facilitates complete filling of the array chamber by an aqueous fluid;
    a waste chamber comprising a waste inlet and an absorbent material; and
    a channel having an expansion section with a first end proximate to the outlet of the array chamber and a second end proximate to the inlet of the waste chamber, wherein the expansion section of the channel has a reversed funnel shape from the first end to the second end, wherein the cross-sectional area of the channel increase continuously in a stepwise manner from the first end of the expansion section to the second end of the expansion section.

2. The microarray assembly of claim 1, wherein the channel further comprises a switchback section between the expansion section and the inlet of the waste chamber.

3. The microarray assembly of claim 2, wherein the switchback section comprises two sharp turns in the channel.

4. The microarray assembly of claim 1, wherein the microarray is an oligonucleotide microarray.

5. The microarray assembly of claim 1, wherein the microarray is a gel spot microarray.

6. The microarray assembly of claim 1, wherein the gel spot array comprises a plurality of gel spots and wherein each gel spot comprises an internal control fluorophore and a capturing agent that binds specifically to the target molecule.

* * * * *